United States Patent
Mattanovich et al.

(10) Patent No.: US 10,428,123 B2
(45) Date of Patent: *Oct. 1, 2019

(54) CONSTITIUTIVE PROMOTER

(71) Applicant: Lonza Ltd., Visp (CH)

(72) Inventors: Diethard Mattanovich, Vienna (AT); Brigitte Gasser, Vienna (AT); Roland Prielhofer, Vienna (AT)

(73) Assignee: Lonza Ltd, Visp (CH)

( * ) Notice: Subject to any disclaimer, the term of this patent is extended or adjusted under 35 U.S.C. 154(b) by 447 days.

This patent is subject to a terminal disclaimer.

(21) Appl. No.: 14/777,400

(22) PCT Filed: Dec. 18, 2013

(86) PCT No.: PCT/EP2013/077144
§ 371 (c)(1),
(2) Date: Sep. 15, 2015

(87) PCT Pub. No.: WO2014/139608
PCT Pub. Date: Sep. 18, 2014

(65) Prior Publication Data
US 2016/0039891 A1    Feb. 11, 2016

Related U.S. Application Data

(63) Continuation of application No. 13/835,589, filed on Mar. 15, 2013, now Pat. No. 9,150,870.

(30) Foreign Application Priority Data

Mar. 15, 2013 (EP) ..................... 13159527

(51) Int. Cl.
*C07K 14/39* (2006.01)
*C12N 15/81* (2006.01)
*C12P 21/00* (2006.01)

(52) U.S. Cl.
CPC ............. *C07K 14/39* (2013.01); *C12N 15/81* (2013.01); *C12N 15/815* (2013.01); *C12P 21/00* (2013.01)

(58) Field of Classification Search
None
See application file for complete search history.

(56) References Cited

U.S. PATENT DOCUMENTS

| | | | |
|---|---|---|---|
| 4,808,537 A | 2/1989 | Stroman et al. | |
| 4,855,231 A | 8/1989 | Stroman et al. | |
| 6,730,499 B1 | 5/2004 | Cregg | |
| 2008/0153126 A1 | 6/2008 | Hartner et al. | |
| 2011/0021378 A1 | 1/2011 | Callewaert et al. | |

FOREIGN PATENT DOCUMENTS

| | | |
|---|---|---|
| CN | 102180954 A | 9/2011 |
| CN | 102994501 A | 3/2013 |
| EP | 0103409 A2 | 3/1984 |
| EP | 1951877 B1 | 11/2010 |
| WO | 9744470 A1 | 11/1997 |
| WO | 2005003310 A2 | 1/2005 |
| WO | 2007015178 A2 | 2/2007 |
| WO | 2014066374 A1 | 5/2014 |
| WO | WO 2014066374 A1 * | 5/2014 ......... C12N 15/1034 |
| WO | 2014138703 A1 | 9/2014 |

OTHER PUBLICATIONS de Schutter et al., Nature Biotechnology, 2009, vol. 27, pp. 561-566.*
DeSchutter et al., Genome sequence of the recombinant protein production host Pichia pastoris, Nature Biotechnol., 27(6):561-566 (2009).
Gasser et al., Engineering of biotin-prototrophy in Pichia pastoris for robust production processes, Metabolic Engineering, 12(6):573-580 (2010).
Marx et al., Directed gene copy number amplication in Pichia pastoris by vector integration into the ribosomal DNA locus, FEMS Yeast Res., 9:1260-1270 (2009).
Mattanovich et al., Genome, secretome and glucose transport highlight unique features of the protein production host Pichia pastoris, Microbial Cell Factories, 8:29 (2009).
Qin et al., GAP Promoter Library for Fine-Tuning of Gene Expression in Pichia pastoris, Applied and Environmental Microbiology, 77:3600-3608 (2011).
Qin et al., Reliable high-throughput approach for screening of engineered constitutive promoters in the yeast *Pichia pastoris*, Letters in Applied Microbiology, 52(6):634-641 (2011).
Stadlmayr et al., Identification and characterisation of novel Pichia pastoris promoters for heterologous protein production, J. Biotechnol., 150(4):519-529 (2010).
Vassileva et al., Expression of hepatitis B surface antigen in the methylotrophic yeast *Pichia pastoris* using the GAP promoter. J. Biotechnol., 88(1):21-35 (2001).
Partial European Search Report for Application No. 13159527.4 dated May 31, 2013.

(Continued)

Primary Examiner — Mindy G Brown
(74) Attorney, Agent, or Firm — Meunier Carlin & Curfman LLC

(57) ABSTRACT

The invention relates to an isolated nucleic acid sequence comprising a promoter, which is a native sequence of *Pichia pastoris* comprising the nucleic acid sequence of pCS1 of SEQ ID 1, or a functionally active variant thereof which is a size variant, a mutant or hybrid of SEQ ID 1, or a combination thereof, expression constructs and recombinant host cells comprising the promoter, and a method of producing a protein of interest under the control of the promoter. It further relates to a method to identify a constitutive promoter from eukaryotic cells, and an isolated nucleic acid sequence comprising a promoter which when operatively linked to a nucleotide sequence encoding a protein of interest directs the expression thereof in a host cell at an expression level that is higher than under control of the native pGAP promoter at high and low growth rates.

15 Claims, 4 Drawing Sheets

Specification includes a Sequence Listing.

(56) References Cited

OTHER PUBLICATIONS

Written Opinion for Application No. PCT/EP2013/077144.
International Search Report for Application No. PCT/EP2013/077144 dated Jan. 21, 2014.
Prielhofer et al., Microbial Cell Factories, Jan. 24, 2013, vol. 12, No. 5, pp. 1-10.
Zhang, Xuanwei et al., "Key regulatory elements of a strong constitutive promoter, Pgcw14, from Pichia pastoris", Biotechnol. Letter (2013), vol. 35, pp. 2113-2119.

* cited by examiner

FIG. 1

SEQ ID 1

AGGGCATCATTGAGGTTTCCACAAAAGGAAGAAACATGGATCCAGAGACATCAACAGAGAGGAAAGCGGGTAGTGA
AGCCGAAGCCACAACACAGCCCGATTTGGAAGGGAGTTCACAATCAAGGTGAGTCCAGCCATTTTTTTCTTTTTT
TTTTTTTTATTCAGGTGAACCCACCTAACTATTTTTAACTGGGATCCAGTGAGCTCGCTGGGTGAAAGCCAACCAT
CTTTTGTTTCGGGGAACCGTGCTCGCCCCGTAAAGTTAATTTTTTTTTCCCGCGCAGCTTTAATCTTTCGGCAGAG
AAGGCGTTTTCATCGTAGCGTGGGAACAGAATAATCAGTTCATGTGCTATACAGGCACATGGCAGCAGTCACTATT
TTGCTTTTTAACCTTAAAGTCGTTCATCAATCATTAACTGACCAATCAGATTTTTTGCATTTGCCACTTATCTAAA
AATACTTTTGTATCTCGCAGATACGTTCAGTGGTTTTCCAGGACAACACCCAAAAAAAGGTATCAATGCCACTAGGC
AGTCGGTTTTATTTTTGGTCACCCACGCAAAGAAGCACCCACCTCTTTTAGGTTTTAAGTTGTGGGAACAGTAACA
CCGCCTAGAGCTTCAGGAAAAACCAGTACCTGTGACCGCAATTCACCATGATGCAGAATGTTAATTTAAACGAGTG
CCAAATCAAGATTTCAACAGACAAATCAATCGATCCATAGTTACCCATTCCAGCCTTTTCGTCGTCGAGCCTGCTT
CATTCCTGCCTCAGGTGCATAACTTTGCATGAAAAGTCCAGATTAGGGCAGATTTTGAGTTTAAAATAGGAAATAT
AAACAAATATACCGCGAAAAAGGTTTGTTTATAGCTTTTCGCCTGGTGCCCGTACGGTATAAATACATACTCTCCTC
CCCCCCCTGGTTCTCTTTTTCTTTTGTTACTTACATTTTACCGTTCCGTCACTCGCTTCACTCAACAACAAAA

SEQ ID 2

GATAGTTCTAGAAGACCTGGCGTCGCTGGTCAACTACTCGTTTCACAAGTTGACAAAGACTTTTACCAAGAGAAGA
GCAGTTGTCACCGACCACAATAACAACCTGGAAGCCGAGAAAAAACTTGGAATCTCCAAGGTGAGACTGCCTAGAA
ATCCGTACTCTGCGGCCGATCGAAGACTGCATTTCCTCCAAGAATTGATGCTCATGGTCTCATCTTACAATCGCAC
ACACAACAGTGTCAGTCTTCTTTGCGGTCCCTGAACACAACCAACCGAAAGGTGGGAAGTCTAATGTCACGCAA
ACGATATTGCAACCAATGTTGGGCTCTACTGGCGTCTGGCTGCATCAAATAGCTGATCGGTTCGTAATCTTCAAAG
ATTGGTGTAGGACGAACGAGTCTGCTGGGCTACAAGTTTTGCCCCATATCGCTGTTCAAGCCAACCCGCGGAATCC
CAAAACACCCCATCCGACAAAAGTTGTTGTTTCAGCAGATCTAGGGAGGGCATCATTGAGGTTTCCACAAAAGGA
AGAAACATGGATCCAGAGACATCAACAGAGAGGAAAGCGGGTAGTGAAGCCGAAGCCACAACACAGCCCGATTTGG
AAGGGAGTTCACAATCAAGGTGAGTCCAGCCATTTTTTTTCTTTTTTTTTTTTTATTCAGGTGAACCCACCTAAC
TATTTTTAACTGGGATCCAGTGAGCTCGCTGGGTGAAAGCCAACCATCTTTTGTTTCGGGGAACCGTGCTCGCCCC
GTAAAGTTAATTTTTTTTCCCGCGCAGCTTTAATCTTTCGGCAGAGAAGGCGTTTTCATCGTAGCGTGGGAACAG
AATAATCAGTTCATGTGCTATACAGGCACATGGCAGCAGTCACTATTTTGCTTTTTAACCTTAAAGTCGTTCATCA
ATCATTAACTGACCAATCAGATTTTTGCATTTGCCACTTATCTAAAAATACTTTTGTATCTCGCAGATACGTTCA
GTGGTTTCCAGGACAACACCCAAAAAAAGGTATCAATGCCACTAGGCAGTCGGTTTTATTTTTGGTCACCCACGCA
AAGAAGCACCCACCTCTTTTAGGTTTTAAGTTGTGGGAACAGTAACACCGCCTAGAGCTTCAGGAAAAACCAGTAC
CTGTGACCGCAATTCACCATGATGCAGAATGTTAATTTAAACGAGTGCCAAATCAAGATTTCAACAGACAAATCAA
TCGATCCATAGTTACCCATTCCAGCCTTTTCGTCGTCGAGCCTGCTTCATTCCTGCCTCAGGTGCATAACTTTGCA
TGAAAAGTCCAGATTAGGGCAGATTTTGAGTTTAAAATAGGAAATATAAACAAATATACCGCGAAAAAGGTTTGTT
TATAGCTTTTCGCCTGGTGCCGTACGGTATAAATACATACTCTCCTCCCCCCCCTGGTTCTCTTTTTCTTTTGTTA
CTTACATTTTACCGTTCCGTCACTCGCTTCACTCAACAACAAAA

SEQ ID 3

AGCCAACCATCTTTTGTTTCGGGGAACCGTGCTCGCCCCGTAAAGTTAATTTTTTTTCCCGCGCAGCTTTAATCT
TTCGGCAGAGAAGGCGTTTTCATCGTAGCGTGGGAACAGAATAATCAGTTCATGTGCTATACAGGCACATGGCAGC
AGTCACTATTTTGCTTTTTAACCTTAAAGTCGTTCATCAATCATTAACTGACCAATCAGATTTTTGCATTTGCCA
CTTATCTAAAAATACTTTTGTATCTCGCAGATACGTTCAGTGGTTTCCAGGACAACACCCAAAAAAAGGTATCAAT
GCCACTAGGCAGTCGGTTTTATTTTTGGTCACCCACGCAAAGAAGCACCCACCTCTTTTAGGTTTTAAGTTGTGGG
AACAGTAACACCGCCTAGAGCTTCAGGAAAAACCAGTACCTGTGACCGCAATTCACCATGATGCAGAATGTTAATT
TAAACGAGTGCCAAATCAAGATTTCAACAGACAAATCAATCGATCCATAGTTACCCATTCCAGCCTTTTCGTCGTC
GAGCCTGCTTCATTCCTGCCTCAGGTGCATAACTTTGCATGAAAAGTCCAGATTAGGGCAGATTTTGAGTTTAAAA
TAGGAAATATAAACAAATATACCGCGAAAAAGGTTTGTTTATAGCTTTTCGCCTGGTGCCGTACGGTATAAATACA
TACTCTCCTCCCCCCCCTGGTTCTCTTTTTCTTTTGTTACTTACATTTTACCGTTCCGTCACTCGCTTCACTCAAC
AACAAAA

FIG. 1 (cont.)

SEQ ID 4

GTGGTTTCCAGGACAACACCCAAAAAAAGGTATCAATGCCACTAGGCAGTCGGTTTTATTTTTGGTCACCCACGCA
AAGAAGCACCCACCTCTTTTAGCTTTTAAGTTCTGGCAACACTAACACCGCCTACAGCTTCAGCAAAAACCAGTAC
CTGTGACCGCAATTCACCATGATGCAGAATGTTAATTTAAACGAGTGCCAAATCAAGATTTCAACAGACAAATCAA
TCGATCCATAGTTACCCATTCCAGCCTTTTCGTCGTCGAGCCTGCTTCATTCCTGCCTCAGGTGCATAACTTTGCA
TGAAAAGTCCAGATTAGGGCAGATTTTGAGTTTAAAATAGGAAATATAAACAAATATACCGCGAAAAAGGTTTGTT
TATAGCTTTTCGCCTGGTGCCGTACGGTATAAATACATACTCTCCTCCCCCCCCTGGTTCTCTTTTTCTTTTGTTA
CTTACATTTTACCGTTCCGTCACTCGCTTCACTCAACAACAAAA

SEQ ID 5

GACCGCAATTCACCATGATGCAGAATGTTAATTTAAACGAGTGCCAAATCAAGATTTCAACAGACAAATCAATCGA
TCCATAGTTACCCATTCCAGCCTTTTCGTCGTCGAGCCTGCTTCATTCCTGCCTCAGGTGCATAACTTTGCATGAA
AAGTCCAGATTAGGGCAGATTTTGAGTTTAAAATAGGAAATATAAACAAATATACCGCGAAAAAGGTTTGTTTATA
GCTTTTCGCCTGGTGCCGTACGGTATAAATACATACTCTCCTCCCCCCCCTGGTTCTCTTTTTCTTTTGTTACTTA
CATTTTACCGTTCCGTCACTCGCTTCACTCAACAACAAAA

SEQ ID 6

AGCCTGCTTCATTCCTGCCTCAGGTGCATAACTTTGCATGAAAAGTCCAGATTAGGGCAGATTTTGAGTTTAAAAT
AGGAAATATAAACAAATATACCGCGAAAAAGGTTTGTTTATAGCTTTTCGCCTGGTGCCGTACGGTATAAATACAT
ACTCTCCTCCCCCCCCTGGTTCTCTTTTTCTTTTGTTACTTACATTTTACCGTTCCGTCACTCGCTTCACTCAACA
ACAAAA

SEQ ID 7

CCGCGAAAAAGGTTTGTTTATAGCTTTTCGCCTGGTGCCGTACGGTATAAATACATACTCTCCTCCCCCCCCTGGT
TCTCTTTTTCTTTTGTTACTTACATTTTACCGTTCCGTCACTCGCTTCACTCAACAACAAAA

SEQ ID 8

CATACTCTCCTCCCCCCCCTGGTTCTCTTTTTCTTTTGTTACTTACATTTTACCGTTCCGTCACTCGCTTCACTCA
ACAACAAAA

FIG. 2

SEQ ID 9

```
ATGCAATTCTCTATCGTCGCTACTTTGGCTCTTGCTGGTTCCGCTCTGGCTGCTTACTCTAACGTAACTTACACTT
ACGAGACTACCATCACCGATGTTGTCACCGAGCTCACCACTTACTGCCCAGAGCCAACCACCTTCGTTCACAAGAA
CAAGACCATCACTGTGACCGCCCCAACCACTTTGACCATCACTGACTGTCCTTGCACCATCTCCAAGACCACCAAG
ATCACCACTGATGTTCCACCAACCACCCACTCCACCCCACACACCACCACCACTCACGTGCCATCTACCTCTACCC
CAGCTCCAACCCACTCTGTTTCTACCATCTCTCACGGTGGTGCTGCTAAGGCTGGTGTTGCTGGTTTGGCCGGTGT
TGCTGCTGCCGCTGCTTACTTCTTGTAA
```

SEQ ID 10

```
MQFSIVATLALAGSALAAYSNVTYTYETTITDVVTELTTYCPEPTTFVHKNKTITVTAPTTLTITDCPCTISKTTK
ITTDVPPTTHSTPHTTTHVPSTSTPAPTHSVSTISHGGAAKAGVAGLAGVAAAAAYFL
```

SEQ ID 11

```
ATGCAATTCTCTATCGTCGCTACTTTGGCTCTTGCTGGTTCCGCTCTGGCTGCTTACTCTAACG
TAACTTACACTTACGAGACTACCATCACCGATGTTGTCACTGAGTTGACCACTTACTGCCCAGA
GCCAACCACCTTTGTTTACAAGAACAAGACCATCACCGTGACTGAGCCAACCACTTTGACCATC
ACTGACTGCCCATGCACCATCTCAAAGACCACCAAGATCACCACTGATGTTCCACCAACCACCC
ACGTCACCCATCCACCACTCACGTGCCATCTACCTCTACCCCAGCTCCAACCCACTCTGTTTC
TACCATCTCTCACGGTGGTGCTGCTAAGGCTGGTGTTGCTGGTTTGGCCGGTGTTGCTGCTGCC
GCTGCTTACTTCTTGTAA
```

SEQ ID 12

```
MQFSIVATLALAGSALAAYSNVTYTYETTITDVVTELTTYCPEPTTFVYKNKTITVTEPTTLTITDCPCTISKTTK
ITTDVPPTTHVTPSTTHVPSTSTPAPTHSVSTISHGGAAKAGVAGLAGVAAAAAYFL
```

FIG. 3

SEQ ID 13

```
CTTTTTTGTAGAAATGTCTTGGTGTCCTCGTCCAATCAGGTAGCCATCTCTGAAATATCTGGCT
CCGTTGCAACTCCGAACGACCTGCTGGCAACGTAAAATTCTCCGGGGTAAAACTTAAATGTGGA
GTAATGGAACCAGAAACGTCTCTTCCCTTCTCTCTCCTTCCACCGCCCGTTACCGTCCCTAGGA
AATTTTACTCTGCTGGAGAGCTTCTTCTACGGCCCCCTTGCAGCAATGCTCTTCCCAGCATTAC
GTTGCGGGTAAAACGGAGGTCGTGTACCCGACCTAGCAGCCCAGGGATGGAAAAGTCCCGGCCG
TCGCTGGCAATAATAGCGGGCGGACGCATGTCATGAGATTATTGGAAACCACCAGAATCGAATA
TAAAAGGCGAACACCTTTCCCAATTTTGGTTTCTCCTGACCCAAAGACTTTAAATTTAATTTAT
TTGTCCCTATTTCAATCAATTGAACAACTATCACCTGCAGGCC
```

CONSTITIUTIVE PROMOTER

The invention refers to an isolated nucleic acid sequence comprising a strong constitutive promoter and a method of producing a protein of interest in a eukaryotic cell culture under the control of such a promoter.

BACKGROUND

Successful production of recombinant proteins has been accomplished with eukaryotic hosts. The most prominent examples are yeasts like *Saccharomyces cerevisiae, Pichia pastoris* or *Hansenula polymorpha*, filamentous fungi like *Aspergillus awamori* or *Trichoderma reesei*, or mammalian cells like e.g. CHO cells. While the production of some proteins is readily achieved at high rates, many other proteins are only obtained at comparatively low levels.

The heterologous expression of a gene in a host organism usually requires a vector allowing stable transformation of the host organism. A vector would provide the gene with a functional promoter adjacent to the 5' end of the coding sequence. The transcription is thereby regulated and initiated by this promoter sequence. Most promoters used up to date have been derived from genes that code for proteins that are usually present at high concentrations in the cell.

EP0103409A2 discloses the use of yeast promoters associated with expression of specific enzymes in the glycolytic pathway, i.e. promoters involved in expression of pyruvate kinase, triosephosphate isomerase, phosphoglucose isomerase, phosphor-glycerate mutase, hexokinase 1 and 2, glucokinase, phosphofructose kinase, aldolase and glycolytic regulation gene.

WO 97/44470 describes yeast promoters from *Yarrowia lipolytica* for the translation elongation factor 1 (TEF1) protein and for the ribosomal protein S7 that are suitable for heterologous expression of proteins in yeast, and EP1951877A1 describes the use of the *P. pastoris* TEF1 promoter for the production of heterologous proteins.

WO2005003310 provides methods for the expression of a coding sequence of interest in yeast using a promoter of the glyceraldehyde-3-phosphate dehydrogenase or phosphoglycerate mutase from oleaginous yeast *Yarrowia lipolytica*.

Promoter sequences derived from genes involved in the methanol metabolic pathway of *Pichia pastoris* are disclosed in U.S. Pat. Nos. 4,808,537 and 4,855,231 (alcohol oxidase AOX1, AOX2) and U.S. Pat. No. 6,730,499B1 (formaldehyde dehydrogenase FLD1). US20080153126A1 includes mutant promoter sequences based on the AOX1 promoter.

The AOX1 promoter is induced only in response to methanol and repressed by other carbon sources, such as glucose or ethanol. Methanol has the disadvantage that it is unsuitable for use in the production of certain products, since it is potentially hazardous for its toxicity and flammability. Therefore, alternatives to the AOX1 promoter are sought.

Vassileva et al. (J. Biotechnol. (2001) 88: 21-35) describe the use of the GAP promoter to express HBsAg in *P. pastoris*, using multicopy expression cassettes as an alternative to the AOX1 promoter. The constitutive system was proposed for continuous culture to permit maintenance of the cells in mid-exponential phase.

Promoters used in *Pichia pastoris* are either tightly regulated (like pAOX or pFLD) being active on specific substrates such as methanol, or they are constitutively active in many different conditions, media and substrates. Among the constitutive ones, especially the GAP and the TEF promoters have been described to be strong, and useful for recombinant protein production.

However, it was shown that the activity of both constitutive promoters is not constantly strong during a fed-batch production process. Especially in the later phases of the process, when cell growth rates are slow, also the activity of the promoters in getting low, thus limiting expression levels of the gene of interest (GOI) and production yields (Stadlmayr et al. 2010. J Biotechnol. 150: 519-529).

Selection of suitable promoters is not intuitive or rational, as even highly abundant glycolytic enzymes such as enolase (ENO), triose phosphate isomerase (TPI) or glucose-6-phosphate isomerase (PGI) do not have promoters that are as strong as pGAP and pTEF (Stadlmayr et al. 2010. J Biotechnol. 150: 519-529; Gasser et al. 2010. Metabolic Engineering 12:573-580).

Qin et al. (Applied and Environmental Microbiology (2011) 3600-3608) describe a GAP promoter library and various mutants with varying activities.

WO2007/015178 A2 describes translational fusion partners capable of inducing secretory production of recombinant proteins, and a *P. pastoris* cDNA library.

CN 102180954 A describes cell surface display system using the *P. pastoris* cell wall protein GCW14 as an anchored protein.

It is desirable to provide improved recombinant eukaryotic cell lines to produce fermentation products that can be isolated with high yields. Therefore, it is the object of the present invention to provide for alternative regulatory elements suitable for recombinant production methods, which are simple and efficient.

SUMMARY OF THE INVENTION

The object is solved by the subject matter as claimed.

According to the invention there is provided an isolated nucleic acid sequence comprising a promoter, which is a native sequence of *Pichia pastoris* comprising or consisting of the pCS1 nucleic acid sequence of SEQ ID 1, or a functionally active variant thereof which is a size variant, a mutant or hybrid of SEQ ID 1, or a combination thereof.

According to a specific aspect, there is provided an isolated nucleic acid sequence comprising a promoter, which is a native sequence of *Pichia pastoris* comprising or consisting of the pCS1 nucleic acid sequence of SEQ ID 1, or a functionally active variant thereof which is a size variant, a mutant or hybrid of SEQ ID 1, or a combination thereof, wherein said functionally active variant exhibits substantially the same activity as pCS1, specifically the pCS1 nucleic acid sequence of SEQ ID 1.

Specifically, the pCS1 nucleotide sequence is identical with the sequence of SEQ ID 1.

Preferably, the nucleic acid sequence of the invention is not identical to the nucleic acid of SEQ ID 87 as listed in WO2007/015178 A2 (i.e. SEQ ID 24 of this application).

Specifically, the functionally active variant is a) a size variant of pCS1 of SEQ ID 1, preferably consisting of or comprising the nucleic acid sequence selected from the group consisting of SEQ ID 2, 3, 4, 5, 6, 7 and 8;

b) a mutant of the pCS1 of SEQ ID 1, or a mutant of the size variant of a), which mutant has at least 60% homology to the sequence SEQ ID 1 or to the size variant;

c) a hybrid comprising
   a sequence selected from the group consisting of pCS1 of SEQ ID 1, a size variant of a), and a mutant of b); and at least one further sequence selected from the group consisting of pCS1 of SEQ ID 1, a size variant of a), a mutant of b), and a heterologous sequence; or d) a sequence which hybridizes under stringent conditions to any of the size variant, or the mutant nucleic acid sequences of a), or b).

Preferably, the size variant of pCS1 of SEQ ID 1 consists of any of SEQ ID 2, SEQ ID 3, SEQ ID 4, SEQ ID 5 or SEQ ID 6

According to a specific embodiment, the functionally active variant is selected from the group consisting of homologs with i) at least about 60% nucleotide sequence identity;

ii) homologs obtainable by modifying the nucleotide sequence of pCS1 of SEQ ID 1 or size variants thereof, by insertion, deletion or substitution of one or more nucleotides within the sequence or at either or both of the distal ends of the sequence, preferably with a nucleotide sequence of 80 bp to 1500 bp, or of 200 bp to 1500 bp, more preferably at least 200 bp; and iii) analogs derived from species other than *Pichia pastoris*.

Specifically the functionally active variant of the invention has substantially the same promoter activity as pCS1.

According to a specific embodiment, the nucleic acid sequence is operably linked to a nucleotide sequence encoding a protein of interest (POI), which nucleic acid is not natively associated with the nucleotide sequence encoding the POI.

According to a specific aspect, the nucleic acid sequence further comprises a signal peptide gene enabling the secretion of the POI, preferably wherein the signal peptide gene is located adjacent to the 5' end of the nucleotide sequence encoding the POI.

Accordingly, the invention specifically refers to the nucleic acid sequence which further comprises a nucleic acid sequence encoding a signal peptide enabling the secretion of the POI, preferably wherein nucleic acid sequence encoding the signal peptide is located adjacent to the 5' end of the nucleotide sequence encoding the POI.

The invention further provides for an expression construct comprising a nucleic acid sequence of the invention, preferably an autonomously replicating vector or plasmid, or one which integrates into the chromosomal DNA of a host cell.

The invention further provides for a recombinant host cell which comprises the nucleic acid sequence of the invention or the expression construct of the invention, preferably a eukaryotic cell, more preferably a yeast or filamentous fungal cell, more preferably a yeast cell of the *Saccharomyces* or *Pichia* genus.

According to a specific aspect, the recombinant host cell comprises multiple copies of the nucleic acid sequence, and/or multiple copies of the expression construct. For example, the recombinant cell comprises 2, 3, 4, or more copies (gene copy number, GCN).

Specifically, the recombinant host cell is selected from the group consisting of mammalian, insect, yeast, filamentous fungi and plant cells, preferably a yeast, preferably any of the *P. pastoris* strains CBS 704, CBS 2612, CBS 7435, CBS 9173-9189, DSMZ 70877, X-33, GS115, KM71 and SMD1168. In some embodiments, the recombinant host cell is a *P. pastoris* strain other than X-33.

The invention further provides for a stable culture of a plurality of the cell of the invention.

The invention further provides for a method of producing a POI by culturing a recombinant host cell line comprising the nucleic acid sequence or the promoter of the invention, or the expression construct of the invention, and a nucleic acid encoding the POI under the transcriptional control of said promoter, comprising the steps of a) cultivating the cell line under conditions to express said POI, and b) recovering the POI.

Specifically, the POI is expressed under growth-limiting conditions, e.g. by cultivating the cell line at a growth rate of less than the maximal growth rate, typically less than 90%, preferably less than 80%, less than 70%, less than 60%, less than 50%, less than 40%, less than 30%, less than 20%, less than 10%, less than 5%, less than 3%, less than 2%, less than 1%, less than 0.5%, less than 0.4%, less than 0.3%, or less than 0.2% of the maximum growth rate of the cells. Typically the maximum growth rate is individually determined for a specific host cell.

According to a specific embodiment, the cell line is cultivated under batch, fed-batch or continuous cultivation conditions, and/or in media containing limited carbon substrate.

Specifically, the cultivation is performed in a bioreactor starting with a batch phase followed by a fed-batch phase or a continuous cultivation phase.

Specifically, the host cells are grown in a carbon source rich medium during the phase of high growth rate (e.g. at least 50%, or at least 60%, at least 70%, at least 80%, at least 90%, at least 95%, at least 98%, at least 99%, or up to the maximum growth rate) and producing the POI during a phase of low growth rate (e.g. less than 90%, preferably less than 80%, less than 70%, less than 60%, less than 50%, or less than 40%, less than 30%, less than 20%, less than 10%, less than 5%, less than 3%, less than 2%, less than 1%, less than 0.5%, less than 0.4%, less than 0.3%, or less than 0.2% of the maximum growth rate) e.g. while limiting the carbon source, preferably by feeding a defined minimal medium. Specifically the defined minimal medium does not comprise a transcription-inducing carbon source.

The POI is specifically a heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI, specifically including a cell metabolite of the recombinant cell culture that expresses a gene of interest under the transcriptional control of a promoter of the invention.

The invention further provides for a method to identify a constitutive promoter from eukaryotic cells, comprising the steps of a) cultivating eukaryotic cells at a high growth rate;

b) further cultivating the cells at a low growth rate;

c) providing samples of the cell culture of step a) and b), d) performing transcription analysis in said samples and comparing the transcript levels with the transcript levels of the native pGAP promoter of the cells; and f) selecting the constitutive promoter that has a higher transcription strength as compared to the native pGAP promoter at high and low growth rates, preferably by determining a transcript level of the identified constitutive promoter which is at least 1.1-fold higher as compared to the native pGAP promoter, preferably at least 1.2-fold, preferably at least 1.3-fold, preferably at least 1.4-fold, preferably at least 1.5-fold, preferably at least 1.6-fold, preferably at least 1.7-fold, preferably at least 1.8-fold, preferably at least 1.9-fold, preferably at least 2-fold, preferably at least 3-fold, preferably at least 4-fold, preferably at least 5-fold, preferably at least 10-fold, or at least 15-fold higher.

Specifically, the transcript level is determined at a high growth rate and a low growth rate within the range of 0.01 to 0.2 $h^{-1}$, preferably within the range of 0.015 to 0.15 $h^{-1}$, e.g. by examining at least two samples of a cell culture, a first one representing a high growth rate, such as at least 0.05 $h^{-1}$, preferably at least 0.06 $h^{-1}$, or at least 0.07 $h^{-1}$, at least 0.08 $h^{-1}$, at least 0.09 $h^{-1}$, at least 0.1 $h^{-1}$, e.g. at a growth rate of 0.15 $h^{-1}$, and a second one representing a low growth rate, such as less than the first one, e.g. less than 0.05 $h^{-1}$, preferably less than 0.04 $h^{-1}$, less than 0.03 $h^{-1}$, or less than 0.02 $h^{-1}$, e.g. at a growth rate of 0.015 $h^{-1}$. The transcription level is specifically determined by analysis of the gene expression patterns using DNA microarrays, e.g. according to Example 11 below.

The invention further provides for the use of an isolated nucleic acid sequence comprising or consisting of a promoter which when operatively linked to a nucleotide sequence encoding a POI directs the expression thereof in a host cell at an expression level that is higher than under control of the native pGAP promoter at high and low growth rates, preferably in a method of producing a POI by cultivating a host cell transformed with the nucleic acid sequence, wherein the cultivation is performed in a bioreactor starting with a batch phase followed by a fed-batch phase or a continuous cultivation phase.

Specifically, the expression level is determined at a high growth rate and a low growth rate within the range of 0.01 to 0.2 $h^{-1}$, preferably within the range of 0.015 to 0.15 $h^{-1}$, e.g. by examining at least two samples of a cell culture, a first one representing a high growth rate, such as at least 0.05 $h^{-1}$, preferably at least 0.06 $h^{-1}$, or at least 0.07 $h^{-1}$, at least 0.08 $h^{-1}$, at least 0.09 $h^{-1}$, at least 0.1 $h^{-1}$, e.g. at a growth rate of 0.15 $h^{-1}$, and a second one representing a low growth rate, such as less than the first one, e.g. less than 0.05 $h^{-1}$, preferably less than 0.04 $h^{-1}$, less than 0.03 $h^{-1}$, or less than 0.02 $h^{-1}$, e.g. at a growth rate of 0.015 $h^{-1}$. The expression level is specifically determined under growth-limited conditions. An example of determining the expression strength in growth-limited conditions e.g. in a glucose-limited chemostat cultivation, at high and low growth rates is provided in Example 10 below.

Specifically, the expression level is at least 1.1-fold higher compared to the pGAP promoter, preferably at least 1.2-fold, preferably at least 1.3-fold, preferably at least 1.4-fold, preferably at least 1.5-fold, preferably at least 1.6-fold, preferably at least 1.7-fold, preferably at least 1.8-fold, preferably at least 1.9-fold, preferably at least 2-fold, preferably at least 3-fold, preferably at least 4-fold, preferably at least 5-fold, preferably at least 10-fold, or at least 15-fold higher.

According to a specific aspect, the isolated nucleic acid sequence of the invention or the expression construct of the invention is used in a method of producing a POI by cultivating a host cell transformed with the nucleic acid sequence and/or the expression construct, preferably wherein the cultivation is performed in a bioreactor starting with a batch phase followed by a fed-batch phase or a continuous cultivation phase.

FIGURES

FIG. 1: Nucleic acid sequence pCS1 (985 bp, SEQ ID 1) of *P. pastoris*, and promoter sequences which are DNA sequences including pCS1 and additional nucleotides at the 5' end, or pCS1 fragments, promoting expression of CS1 in *P. pastoris*, which comprise 1488 bp (SEQ ID 2), 767 bp (SEQ ID 3), 500 bp (SEQ ID 4), 344 bp (SEQ ID 5), 234 bp (SEQ ID 6), 138 bp (SEQ ID 7) and 85 bp (SEQ ID 8).

FIG. 2: Sequences of CS1 coding nucleotide sequence and amino acid sequence
   i) of strains GS115, CBS7435 and CBS2612 (PAS_chr1-4_0586), coding sequence (SEQ ID 9), translated sequence (XM_002490678.1, SEQ ID 10); and
   ii) of strain DSMZ70382 (PIPA02805), coding sequence (SEQ ID 11), translated sequence (SEQ ID 12).

FIG. 3: Native pGAP promoter sequence of *P. pastoris* (GS115) (SEQ ID 13).

DETAILED DESCRIPTION OF THE INVENTION

Specific terms as used throughout the specification have the following meaning.

The term "carbon source" or "carbon substrate" as used herein shall mean a fermentable carbon substrate, typically a source carbohydrate, suitable as an energy source for microorganisms, such as those capable of being metabolized by host organisms or production cell lines, in particular sources selected from the group consisting of monosaccharides, oligosaccharides, polysaccharides, alcohols including glycerol, in the purified form, in minimal media or provided in raw materials, such as a complex nutrient material. The carbon source may be used according to the invention as a single carbon source or as a mixture of different carbon sources.

The term "carbon substrate rich conditions" as used herein specifically refers to the type and amount of a carbon substrate suitable for cell growth, such as a nutrient for eukaryotic cells. The carbon source may be provided in a medium, such as a basal medium or complex medium, but also in a (chemically) defined medium containing a purified carbon source. The carbon source for use in a growth phase of a cell cultivation process is herein also called "basal carbon source" and typically provided in an amount to provide for cell growth, for example to obtain cell densities of at least 5 g/L cell dry mass, preferably at least 10 g/L cell dry mass, or at least 15 g/L cell dry mass, e.g. exhibiting viabilities of more than 90% during standard sub-culture steps, preferably more than 95%.

In a growth phase, the carbon source is typically used in an excess or surplus amount, which is understood as an excess providing energy to increase the biomass, e.g. during the cultivation of a cell line with a high specific growth rate.

This surplus amount is particularly in excess of the limited amount of a carbon source as used under growth-limited conditions, to achieve a residual concentration in the fermentation broth that is measurable and typically at least 10-fold higher, preferably at least 50-fold or at least 100-fold higher than during feeding the cell culture with a medium containing limited carbon substrate.

The term "carbon substrate limited conditions" or "limited carbon source", herein also referred to as "supplemental carbon source", such as used according to the invention is herein understood to specifically refer to the type and amount of a carbon substrate facilitating the production of fermentation products by production cell lines, in particular in a cultivation process with controlled growth rates of less than the maximum growth rate. The production phase specifically follows a growth phase, e.g. in batch, fed-batch and continuous cultivation process.

In general, cell culture processes are classified into batch culture, continuous culture, and fed-batch culture. Batch culture is a culture process by which a small amount of a seed culture solution is added to a medium and cells are grown without adding an additional medium or discharging a culture solution during culture. Continuous culture is a culture process by which a medium is continuously added and discharged during culture. The continuous culture also includes perfusion culture. Fed-batch culture, which is an intermediate between the batch culture and the continuous culture and also referred to as semi-batch culture, is a culture process by which a medium is continuously or sequentially added during culture but, unlike the continuous culture, a culture solution is not continuously discharged.

Specifically preferred is a fed-batch process which is based on feeding of a growth limiting nutrient substrate to a culture. The fed-batch strategy, including single fed-batch or repeated fed-batch fermentation, is typically used in bio-industrial processes to reach a high cell density in the bioreactor. The controlled addition of the carbon substrate directly affects the growth rate of the culture and helps to avoid overflow metabolism or the formation of unwanted metabolic byproducts. Under carbon source limited conditions, the carbon source specifically may be contained in the feed of a fed-batch process. Thereby, the carbon substrate is provided in a limited amount.

Also in chemostat or continuous culture as described herein, the growth rate can be tightly controlled.

A "limited amount" of a carbon source is herein understood as the amount of a carbon source necessary to keep a production cell line under growth-limited conditions, e.g. in a production phase or production mode. Such a limited amount may be employed in a fed-batch process, where the carbon source is contained in a feed medium and supplied to the culture at low feed rates for sustained energy delivery, e.g. to produce a POI, while keeping the biomass at low specific growth rates. A feed medium is typically added to a fermentation broth during the production phase of a cell culture.

The limited amount of a carbon source may, for example, be determined by the residual amount of the carbon source in the cell culture broth, which is below a predetermined threshold or even below the detection limit as measured in a standard (carbohydrate) assay. The residual amount typically would be determined in the fermentation broth upon harvesting a fermentation product.

The limited amount of a carbon source may as well be determined by defining the average feed rate of the carbon source to the fermenter, e.g. as determined by the amount added over the full cultivation process, e.g. the fed-batch phase, per cultivation time, to determine a calculated average amount per time. This average feed rate is kept low to ensure complete usage of the supplemental carbon source by the cell culture, e.g. between 0.6 g $L^{-1}$ $h^{-1}$ (g carbon source per L initial fermentation volume and h time) and 25 g $L^{-1}$ $h^{-1}$, preferably between 1.6 g $L^{-1}$ $h^{-1}$ and 20 g $L^{-1}$ $h^{-1}$.

The limited amount of a carbon source may also be determined by measuring the specific growth rate, which specific growth rate is kept low, e.g. lower than the maximum specific growth rate, during the production phase, e.g. within a predetermined range, such as in the range of 0.001 $h^{-1}$ to 0.20 $h^{-1}$, or 0.02 $h^{-1}$ to 0.20 $h^{-1}$, preferably between 0.02 $h^{-1}$ and 0.15 $h^{-1}$.

Any type of organic carbon suitable used for eukaryotic cell culture may be used. According to a specific embodiment, the carbon source is a hexose such as glucose, fructose, galactose or mannose, a disaccharide, such as saccharose, an alcohol, such as glycerol or ethanol, or a mixture thereof.

According to a specifically preferred embodiment, the basal carbon source is selected from the group consisting of glucose, glycerol, ethanol, or mixtures thereof, and complex nutrient material. According to a preferred embodiment, the basal carbon source is glycerol.

According to a further specific embodiment, a supplemental carbon source is a hexose such as glucose, fructose, galactose and mannose, a disaccharide, such as saccharose, an alcohol, such as glycerol or ethanol, or a mixture thereof. According to a preferred embodiment, a supplemental carbon source is glucose.

Specifically, the method may employ glycerol as a basal carbon source and glucose as a supplemental carbon source.

Specifically, a feed medium as used herein is chemically defined and methanol-free.

The term "chemically defined" or "defined" with respect to cell culture medium, such as a minimal medium or feed medium in a fed-batch process, shall mean a cultivation medium suitable for the in vitro cell culture of a production cell line, in which all of the chemical components and (poly)peptides are known. Typically a chemically defined medium is entirely free of animal-derived components and represents a pure and consistent cell culture environment.

The term "cell line" as used herein refers to an established clone of a particular cell type that has acquired the ability to proliferate over a prolonged period of time. The term "host cell line" refers to a cell line as used for expressing an endogenous or recombinant gene or products of a metabolic pathway to produce polypeptides or cell metabolites mediated by such polypeptides. A "production host cell line" or "production cell line" is commonly understood to be a cell line ready-to-use for cultivation in a bioreactor to obtain the product of a production process, such as a POI. The term "eukaryotic host" or "eukaryotic cell line" shall mean any eukaryotic cell or organism, which may be cultivated to produce a POI or a host cell metabolite. It is well understood that the term does not include human beings.

According to specifically preferred eukaryotic host cells of the invention, the cell or cell line is selected from the group consisting of mammalian, insect, yeast, filamentous fungi and plant cell lines, preferably a yeast.

Specifically the yeast is selected from the group consisting of *Pichia, Candida, Torulopsis, Arxula, Hensenula, Yarrowia, Kluyveromyces, Saccharomyces, Komagataella*, preferably a methylotrophic yeast.

A specifically preferred yeast is *Pichia pastoris, Komagataella pastoris, K. phaffii*, or *K. pseudopastoris*.

The term "cell culture" or "cultivation", also termed "fermentation", with respect to a host cell line is meant the maintenance of cells in an artificial, e.g., an in vitro environment, under conditions favoring growth, differentiation or continued viability, in an active or quiescent state, of the cells, specifically in a controlled bioreactor according to methods known in the industry.

When cultivating a cell culture using the culture media of the present invention, the cell culture is brought into contact with the media in a culture vessel or with substrate under conditions suitable to support cultivation of the cell culture. In certain embodiments, a culture medium as described herein is used to culture cells according to standard cell culture techniques that are well-known in the art. In various aspects of the invention, a culture medium is provided that can be used for the growth of eukaryotic cells, specifically yeast or filamentous fungi.

Cell culture media provide the nutrients necessary to maintain and grow cells in a controlled, artificial and in vitro environment. Characteristics and compositions of the cell culture media vary depending on the particular cellular requirements. Important parameters include osmolality, pH, and nutrient formulations. Feeding of nutrients may be done in a continuous or discontinuous mode according to methods known in the art. The culture media used according to the invention are particularly useful for producing recombinant proteins.

Whereas a batch process is a cultivation mode in which all the nutrients necessary for cultivation of the cells are contained in the initial culture medium, without additional supply of further nutrients during fermentation, in a fed-batch process, after a batch phase, a feeding phase takes place in which one or more nutrients are supplied to the culture by feeding. The purpose of nutrient feeding is to increase the amount of biomass in order to increase the amount of recombinant protein as well. Although in most cultivation processes the mode of feeding is critical and important, the present invention employing the promoter of the invention is not restricted with regard to a certain mode of cultivation.

In certain embodiments, the method of the invention is a fed-batch process. Specifically, a host cell transformed with a nucleic acid construct encoding a desired recombinant POI, is cultured in a growth phase medium and transitioned to a production phase medium in order to produce a desired recombinant POI.

The feed medium may be added to the culture medium in the liquid form or else in an alternative form, such as a solid, e.g. as a tablet or other sustained release means, or a gas, e.g. carbon dioxide. Yet, according to a preferred embodiment the limited amount of a supplemental carbon source added to the cell culture medium, may even be zero. Preferably, under conditions of a limited carbon substrate, the concentration of a supplemental carbon source in the culture medium is 0-1 g/L, preferably less than 0.6 g/L, more preferred less than 0.3 g/L, more preferred less than 0.1 g/L, preferably 1-50 mg/L, more preferred 1-10 mg/L, specifically preferred 1 mg/L or even below, such as below the detection limit as measured with a suitable standard assay, e.g. determined as a residual concentration in the culture medium upon consumption by the growing cell culture.

In a preferred method, the limited amount of the carbon source provides for a residual amount in the cell culture which is below the detection limit as determined in the fermentation broth at the end of a production phase or in the output of a fermentation process, preferably upon harvesting the fermentation product.

Preferably, the limited amount of a supplemental carbon source is growth limiting to keep the specific growth rate lower than the maximum specific growth rate, such as in the range of 0.001 $h^{-1}$ to 0.20 $h^{-1}$, or 0.02 $h^{-1}$ to 0.20 $h^{-1}$, preferably between 0.02 $h^{-1}$ and 0.15 $h^{-1}$.

In another embodiment, host cells of the present invention are cultivated in continuous mode, e.g. a chemostat. A continuous fermentation process is characterized by a defined, constant and continuous rate of feeding of fresh culture medium into the bioreactor, whereby culture broth is at the same time removed from the bioreactor at the same defined, constant and continuous removal rate. By keeping culture medium, feeding rate and removal rate at the same constant level, the cultivation parameters and conditions in the bioreactor remain constant.

A stable cell culture as described herein is specifically understood to refer to a cell culture maintaining the genetic properties, specifically keeping the POI production level high, e.g. at least at a μg level, even after about 20 generations of cultivation, preferably at least 30 generations, more preferably at least 40 generations, most preferred of at least 50 generations. Specifically, a stable recombinant host cell line is provided which is considered a great advantage when used for industrial scale production.

The cell culture of the invention is particularly advantageous for methods on an industrial manufacturing scale, e.g. with respect to both the volume and the technical system, in combination with a cultivation mode that is based on feeding of nutrients, in particular a fed-batch or batch process, or a continuous or semi-continuous process (e.g. chemostat).

The term "expression" or "expression system" or "expression cassette" refers to nucleic acid molecules containing a desired coding sequence and control sequences in operable linkage, so that hosts transformed or transfected with these sequences are capable of producing the encoded proteins or host cell metabolites. In order to effect transformation, the expression system may be included in a vector; however, the relevant DNA may also be integrated into the host chromosome. Expression may refer to secreted or non-secreted expression products, including polypeptides or metabolites.

"Expression constructs" or "vectors" or "plasmid" used herein are defined as DNA sequences that are required for the transcription of cloned recombinant nucleotide sequences, i.e. of recombinant genes and the translation of their mRNA in a suitable host organism. Expression vectors or plasmids usually comprise an origin for autonomous replication in the host cells, selectable markers (e.g. an amino acid synthesis gene or a gene conferring resistance to antibiotics such as zeocin, kanamycin, G418 or hygromycin), a number of restriction enzyme cleavage sites, a suitable promoter sequence and a transcription terminator, which components are operably linked together. The terms "plasmid" and "vector" as used herein include autonomously replicating nucleotide sequences as well as genome integrating nucleotide sequences.

The expression construct of the invention specifically comprises a promoter of the invention, operably linked to a nucleotide sequence encoding a POI under the transcriptional control of said promoter, which promoter is not natively associated with the coding sequence of the POI.

The term "heterologous" as used herein with respect to a nucleotide or amino acid sequence or protein, refers to a compound which is either foreign, i.e. "exogenous", such as not found in nature, to a given host cell; or that is naturally found in a given host cell, e.g., is "endogenous", however, in the context of a heterologous construct, e.g. employing a heterologous nucleic acid. The heterologous nucleotide sequence as found endogenously may also be produced in an unnatural, e.g. greater than expected or greater than naturally found, amount in the cell. The heterologous nucleotide sequence, or a nucleic acid comprising the heterologous nucleotide sequence, possibly differs in sequence from the endogenous nucleotide sequence but encodes the same protein as found endogenously. Specifically, heterologous nucleotide sequences are those not found in the same relationship to a host cell in nature. Any recombinant or artificial nucleotide sequence is understood to be heterologous. An example of a heterologous polynucleotide is a nucleotide sequence not natively associated with the promoter according to the invention, e.g. to obtain a hybrid promoter, or operably linked to a coding sequence, as described herein. As a result, a hybrid or chimeric polynucleotide may be obtained. A further example of a heterologous compound is a POI encoding polynucleotide operably linked to a transcriptional control element, e.g., a promoter of the invention, to which an endogenous, naturally-occurring POI coding sequence is not normally operably linked.

The term "variant" as used herein in the context of the present invention shall specifically refer to any sequence derived from a parent sequence, e.g. by size variation, e.g. elongation or fragmentation, mutation, hybridization (including combination of sequences), or with a specific degree of homology, or analogy.

The invention specifically provides for a promoter which is a wild-type promoter, e.g. of *P. pastoris*, or a functionally active variant thereof, e.g. capable of controlling the transcription of a specific gene in a wild-type or recombinant eukaryotic cell.

The term "native" as used herein in the context of the present invention shall specifically refer to an individual structure or component of an organism, which is naturally associated with its environment. It is, however, well understood, that native structures or components may be isolated from the naturally associated environment, and provided as isolated native structures or components. Such isolated native structures or components may as well be of artificial or synthetic origin, and still have the same characteristics as the ones of natural origin.

Though some embodiments of the present invention refer to native structures or components, e.g. in the isolated form, it is well understood that the materials, methods and uses of the invention, e.g. specifically referring to isolated nucleic acid sequences, amino acid sequences, expression constructs, transformed host cells and recombinant proteins, are "man-made" and are therefore not considered as a result of "law of nature".

The functionally active variant promoter may e.g. be derived from the promoter sequence pCS1 (SEQ ID 1) by mutagenesis, thus employing the pCS1 sequence as a "parent" sequence, to produce sequences suitable for use as a promoter in recombinant cell lines. Such variant promoter may be obtained from a (pCS1) library of mutant sequences by selecting those library members with predetermined properties. Variant promoters may have the same or even improved properties, e.g. improved in promoter strength to support POI production, still with substantially the same promoter function and strength at high and low growth rates, specifically understood herein as "growth-rate independent function".

The variant promoter may also be derived from analogous sequences, e.g. from eukaryotic species other than *Pichia pastoris* or from a genus other than *Pichia*, such as from *K. lactis, Z. rouxii, P. stipitis, H. polymorpha*. Specifically, the analogous promoter sequences natively associated with genes analogous to the corresponding *P. pastoris* genes may be used as such or as parent sequences to produce functionally active variants thereof. Specifically, a promoter analogous to pCS1 is characterised that it is natively associated with a gene analogous to CS1 (see amino acid sequence of SEQ ID 9 or 11). The properties of such analogous promoter sequences or functionally active variants thereof may be determined using standard techniques.

The "functionally active" variant of a nucleotide or promoter sequence as used herein specifically means a mutant sequence, e.g. resulting from modification of a parent sequence by insertion, deletion or substitution of one or more nucleotides within the sequence or at either or both of the distal ends of the sequence, and which modification does not affect (in particular impair) the activity of this sequence.

Specifically, the functionally active variant of the promoter sequence according to the invention is selected from the group consisting of homologs with at least about 60% nucleotide sequence identity, preferably at least 70%, at least 80%, or at least 90% degree of homology or sequence identity to the parent sequence; and/or homologs obtainable by modifying the parent nucleotide sequence, such as the pCS1 sequence or the sequence of a size variant used as a template to provide for mutations, e.g. by insertion, deletion or substitution of one or more nucleotides within the sequence or at either or both of the distal ends of the sequence, preferably with (i.e. comprising or consisting of) a nucleotide sequence of 80 bp to 1500 bp or of 200 bp to-1500 bp or 234 bp to 1488 bp, preferably at least 100 bp, at least 200 bp, preferably at least 300 bp, more preferred at least 400 bp, at least 500 bp, at least 600 bp, at least 700 bp, at least 800 bp, at least 900 bp, or at least 1000 bp; and analogs derived from species other than *Pichia pastoris*.

Specifically preferred functionally active variants are those derived from a promoter according to the invention by modification, extension and/or fragments of the promoter sequence, with (i.e. comprising or consisting of) a nucleotide sequence of at least 80 bp, preferably at least 100 bp, preferably at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp, preferably up to 1500 bp.

A functionally active variant of a parent promoter sequences as described herein may specifically obtained through mutagenesis methods. The term "mutagenesis" as used in the context of the present invention shall refer to a method of providing mutants of a nucleotide sequence, e.g. through insertion, deletion and/or substitution of one or more nucleotides, so to obtain variants thereof with at least one change in the non-coding or coding region. Mutagenesis may be through random, semi-random or site directed mutation. Typically large randomized gene libraries are produced with a high gene diversity, which may be selected according to a specifically desired genotype or phenotype.

Some of the preferred functionally active variants of the promoter according to the invention are size variants or specifically fragments of pCS1, preferably those including the 3' end of a promoter nucleotide sequence, e.g. a nucleotide sequence derived from one of the promoter nucleotide sequences which has of a specific length and insertions or a deletion of the 5' terminal region, e.g. an elongation or cut-off of the nucleotide sequence at the 5' end, so to obtain a specific length with a range from the 3' end to a varying 5' end, such as with a length of the nucleotide sequence of at least 80 bp, preferably at least 100 bp, preferably at least 200 bp, preferably at least 250 bp, preferably at least 300 bp, more preferred at least 400 bp, at least 500 bp, at least 600 bp, at least 700 bp, at least 800 bp, at least 900 bp, or at least 1000 bp.

The elongated size variant of the invention preferably comprises additional one or more nucleotide(s) at the 5' end of the pCS1 sequence, e.g. those which are natively associated with the wild-type pCS1 sequence in the cell of origin.

For example, a functionally active variant of pCS1 may comprise a nucleotide sequence or consist of a nucleotide sequence selected from the group consisting of pCS1a (SEQ ID 2), pCS1b (SEQ ID 3), pCS1c (SEQ ID 4), pCS1d (SEQ ID 5), pCS1e (SEQ ID 6), pCS1f (SEQ ID 7), and pCS1g (SEQ ID 8), thus, a nucleotide sequence within the range of 80-1500 bp. Preferably, the functionally active variant of pCS1 comprises or consists of a nucleotide sequence selected from the group consisting of pCS1a (SEQ ID 2), pCS1b (SEQ ID 3), pCS1c (SEQ ID 4), pCS1d (SEQ ID 5) and pCS1e (SEQ ID 6).

The functionally active variant of a promoter of the invention is also understood to encompass hybrids of the pCS1 or any of the functionally active variants thereof, in particular any of the parent size variant or fragment sequences, e.g. resulting from combination with one or more of any of the sequences that qualify as pCS1 or functionally active variants thereof, e.g. at least two of such parent sequences, at least 3, at least 4 or at least 5 of the sequences, e.g. a combination of two or more of the pCS1 elongated sequences or fragments selected from the group consisting of pCS1a, pCS1b, pCS1c, pCS1d, pCS1e, pCS1f, and pCS1g; preferably, selected from the group consisting of pCS1a, pCS1b, pCS1c, pCS1d, and pCS1e. In another embodiment, the hybrid is composed of at least one of the sequences selected from pCS1 or any of the functionally active variants thereof, in particular any of the size variant or fragment sequences, and a heterologous sequences which is e.g. not natively associated with the pCS1 sequence in *P. pastoris*.

The functionally active variant of a promoter of the invention is further understood to encompass a nucleotide sequence which hybridizes under stringent conditions to the pCS1 promoter or any of the functionally active size variants or fragments, mutants or hybrid nucleic acid sequences thereof.

As used in the present invention, the term "hybridization" or "hybridizing" is intended to mean the process during which two nucleic acid sequences anneal to one another with stable and specific hydrogen bonds so as to form a double strand under appropriate conditions. The hybridization between two complementary sequences or sufficiently complementary sequences depends on the operating conditions that are used, and in particular the stringency. The stringency may be understood to denote the degree of homology; the higher the stringency, the higher percent homology between the sequences. The stringency may be defined in particular by the base composition of the two nucleic sequences, and/or by the degree of mismatching between these two nucleic sequences. By varying the conditions, e.g. salt concentration and temperature, a given nucleic acid sequence may be allowed to hybridize only with its exact complement (high stringency) or with any somewhat related sequences (low stringency). Increasing the temperature or decreasing the salt concentration may tend to increase the selectivity of a hybridization reaction.

As used in the present invention the phrase "hybridizing under stringent hybridizing conditions" is preferably understood to refer to hybridizing under conditions of certain stringency. In a preferred embodiment the "stringent hybridizing conditions" are conditions where homology of the two nucleic acid sequences is at least 70%, preferably at least 80%, preferably at least 90%, i.e. under conditions where hybridization is only possible if the double strand obtained during this hybridization comprises preferably at least 70%, preferably at least 80%, preferably at least 90% of A-T bonds and C-G bonds.

The stringency may depend on the reaction parameters, such as the concentration and the type of ionic species present in the hybridization solution, the nature and the concentration of denaturing agents and/or the hybridization temperature. The appropriate conditions can be determined by those skilled in the art, e.g. as described in Sambrook et al. (Molecular Cloning: A Laboratory Manual, Cold Spring Harbor, 1989).

The functionally active variant of the invention is specifically characterized by exhibiting substantially the same activity as pCS1.

The term "substantially the same activity" as used herein specifically refers to the activity as indicated by substantially the same or improved promoter strength, specifically the expression or transcriptional strength of the promoter, and its substantially the same or improved characteristics with respect to the promoter strength, specifically determined independent of the growth rate of the host cell such as an expression or transcriptional strength substantially the same as pCS1, e.g. +/−20% or +/−10%, and/or higher than the native pGAP promoter of the host cell, e.g. an at least 1.1-fold increase, or an at least 1.2-fold increase, preferably at least 1.3-fold, preferably at least 1.4-fold, preferably at least 1.5-fold, preferably at least 1.6-fold, preferably at least 1.7-fold, preferably at least 1.8-fold, preferably at least 1.9-fold, and preferably at least 2-fold increase relative to the pGAP promoter strength, or even higher, e.g. at least 3-fold, at least 4-fold, at least 5-fold, at least 10-fold, or at least up to a 15-fold activity, as determined in a suitable test system employing the same type of a host cell, the same cultivation conditions and the same nucleic acid encoding an expression product such as a POI.

The term "homology" indicates that two or more nucleotide sequences have the same or conserved base pairs at a corresponding position, to a certain degree, up to a degree close to 100%. A homologous sequence of the invention typically has at least about 60% nucleotide sequence identity, preferably at least about 70% identity, more preferably at least about 80% identity, more preferably at least about 90% identity, more preferably at least about 95% identity, more preferably at least about 98% or 99% identity.

The homologous promoter sequence according to the invention preferably has a certain homology to any of the pCS1, pCS1a, pCS1b, pCS1c, pCS1d, pCS1e, pCS1f, and pCS1g promoter nucleotide sequences of *P. pastoris* in at least specific parts of the nucleotide sequence, such as including the 3' region of the respective promoter nucleotide sequence, preferably a part with a specific length up to the 3' end of the respective promoter nucleotide sequence, such as a part with a length of 80 bp to 1500 bp, preferably of 200 bp to 1500 bp, more preferably of 234 to 1488 bp; preferably at least 100 bp, preferably at least 200 bp, preferably at least 300 bp, more preferred at least 400 bp, at least 500 bp, at least 600 bp, at least 700 bp, at least 800 bp, at least 900 bp, or at least 1000 bp, and analogs derived from species other than *Pichia pastoris*. Specifically at least those parts are preferably homologous within the range of 300-1000 bp, including the 3' terminal sequence of the respective promoter nucleotide sequence.

Analogous sequences are typically derived from other species or strains. It is expressly understood that any of the analogous promoter sequences of the present invention that are derived from species other than *Pichia pastoris* may comprise a homologous sequence, i.e. a sequence with a certain homology as described herein. Thus, the term "homologous" may also include analogous sequences. On the other hand, it is understood that the invention also refers to analogous sequences and homologs thereof that comprise a certain homology.

"Percent (%) identity" with respect to the nucleotide sequence of a gene is defined as the percentage of nucleotides in a candidate DNA sequence that is identical with the nucleotides in the DNA sequence, after aligning the sequence and introducing gaps, if necessary, to achieve the maximum percent sequence identity, and not considering any conservative substitutions as part of the sequence identity. Alignment for purposes of determining percent nucleotide sequence identity can be achieved in various ways that are within the skill in the art, for instance, using publicly available computer software. Those skilled in the art can determine appropriate parameters for measuring alignment, including any algorithms needed to achieve maximal alignment over the full length of the sequences being compared.

The term "isolated" or "isolation" as used herein with respect to a nucleic acid, a POI or other compound shall refer to such compound that has been sufficiently separated from the environment with which it would naturally be associated, so as to exist in "substantially pure" form. "Isolated" does not necessarily mean the exclusion of artificial or synthetic mixtures with other compounds or materials, or the presence of impurities that do not interfere with the fundamental activity, and that may be present, for example, due to incomplete purification. In particular, isolated nucleic acid molecules of the present invention are also meant to include those chemically synthesized. With reference to nucleic acids of the invention, the term "isolated nucleic acid" or "isolated nucleic acid sequence" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. Specifically, the term "isolated nucleic acid" according to the invention excludes that the pCS1 sequence is linked to a nucleic acid encoding the CS1 protein. An "isolated nucleic acid" (either DNA or RNA) may further represent a molecule produced directly by biological or synthetic means and separated from other components present during its production.

The term "operably linked" as used herein refers to the association of nucleotide sequences on a single nucleic acid molecule, e.g. a vector, in a way such that the function of one or more nucleotide sequences is affected by at least one other nucleotide sequence present on said nucleic acid molecule. For example, a promoter is operably linked with a coding sequence of a recombinant gene, when it is capable of effecting the expression of that coding sequence. As a further example, a nucleic acid encoding a signal peptide is operably linked to a nucleic acid sequence encoding a POI, when it is capable of expressing a protein in the secreted form, such as a preform of a mature protein or the mature protein. Specifically such nucleic acids operably linked to each other may be immediately linked, i.e. without further elements or nucleic acid sequences in between the nucleic acid encoding the signal peptide and the nucleic acid sequence encoding a POI.

The term "promoter" as used herein refers to a DNA sequence capable of controlling the expression of a coding sequence or functional RNA. Promoter activity may be assessed by its transcriptional efficiency. This may be determined directly by measurement of the amount of mRNA transcription from the promoter, e.g. by Northern Blotting or indirectly by measurement of the amount of gene product expressed from the promoter.

The promoter of the invention specifically initiates, regulates, or otherwise mediates or controls the expression of a coding DNA. Promoter DNA and coding DNA may be from the same gene or from different genes, and may be from the same or different organisms.

The promoter of the invention is specifically understood as a constitutive promoter, i.e. a promoter which controls expression without the need for induction, or the possibility of repression. Therefore, there is continuous and steady expression at a certain level. Because of the unique function of high promoter strength at all growth phases or growth rates of the host cell, the constitutive promoter of the invention is particularly useful in a fed-batch culture of the host cell line. Constitutive promoters of the prior art had the disadvantage of low strength at growth-limited conditions, e.g. in fed-batch processes, or were used in embodiments where the host cells were maintained at a high growth rate, e.g. in the mid-exponential phase.

The strength of the promoter of the invention specifically refers to its transcription strength, represented by the efficiency of initiation of transcription occurring at that promoter with high or low frequency. The higher transcription strength the more frequently transcription will occur at that promoter. Promoter strength is important, because it determines how often a given mRNA sequence is transcribed, effectively giving higher priority for transcription to some genes over others, leading to a higher concentration of the transcript. A gene that codes for a protein that is required in large quantities, for example, typically has a relatively strong promoter. The RNA polymerase can only perform one transcription task at a time and so must prioritize its work to be efficient. Differences in promoter strength are selected to allow for this prioritization. According to the invention the promoter is relatively strong independent of the metabolism or the growth rate of the host cell, e.g. both, during in phases of high and low growth rates of a cell culture and specifically independent of the carbon source, exhibiting a state of about maximal activity, specifically at about a constant level.

The relative strength is commonly determined with respect to a standard promoter, such as the respective pGAP promoter of the cell used as the host cell. The frequency of transcription is commonly understood as the transcription rate, e.g. as determined by the amount of a transcript in a suitable assay, e.g. RT-PCR or Northern blotting. The strength of a promoter to express a gene of interest is commonly understood as the expression strength or the capability of support a high expression level/rate. For example, the expression and/or transcription strength of a promoter of the invention is determined in the host cell which is *P. pastoris* and compared to the native pGAP promoter of *P. pastoris*.

The transcription rate may be determined by the transcription strength on a microarray, or with quantitative real time PCR (qRT-PCR) where microarray or qRT-PCR data show the difference of expression level between conditions with high growth rate and conditions with low growth rate, or conditions employing different media composition, and a high signal intensity as compared to the native pGAP promoter. A suitable test system is specifically described in Example 11 below.

The promoter of the invention exerts a relatively high transcription strength, reflected by a transcription rate or transcription strength of at least 110% as compared to the native pGAP promoter in the host cell, sometimes called "homologous pGAP promoter". Preferably the transcription rate or strength is at least 110%, preferably at least 120%, or at least 130%, in specifically preferred cases at least 140%, at least 150%, at least 160%, at least 170%, at least 180%, at least 190%, at least 200%, at least about 3-fold, at least about 4-fold, at least about 5-fold, at least about 10-fold, or at least about 15-fold, or even higher as compared to the native pGAP promoter, e.g. determined in the eukaryotic cell selected as host cell for producing the POI, such as determined under carbon substrate rich conditions, e.g. batch cultures, or under carbon substrate limited conditions, e.g. chemostat or fed batch cultivations.

Preferably the transcription analysis is quantitative or semi-quantitative, preferably employing qRT-PCR, DNA microarrays, RNA sequencing and transcriptome analysis.

The expression rate may, for example, be determined by the amount of expression of a reporter gene, such as eGFP, e.g. as described in the Example section below, a test system is specifically described in Example 10. It could be shown that the pCS1 promoter has a relatively high transcription rate of at least 110% as compared to the native pGAP promoter, upon cultivating a clone in solution.

The promoter of the invention exerts relatively high expression strength, reflected by an expression level of gene of interest, which is at least 110% as compared to the native pGAP promoter in the host cell, sometimes called "homologous pGAP promoter". Preferably the expression strength is at least 110%, preferably at least 120%, or at least 130%, in specifically preferred cases at least 140%, at least 150%, at least 160%, at least 170%, at least 180%, at least 190%, at least 200%, at least about 3-fold, at least about 4-fold, at least about 5-fold, at least about 10-fold, or at least about 15-fold, or even higher as compared to the native pGAP promoter, e.g. determined in the eukaryotic cell selected as host cell for producing the POI, such as determined under carbon substrate rich conditions, e.g. batch cultures, or under carbon substrate limited conditions, e.g. chemostat or fed batch cultivations.

The native pGAP promoter initiates expression of the gap gene encoding glyceraldehyde-3-phosphate dehydrogenase (GAPDH), which is a constitutive promoter present in most living organisms. GAPDH (EC 1\2\1\12), a key enzyme of glycolysis and gluconeogenesis, plays a crucial role in catabolic and anabolic carbohydrate metabolism. Therefore, the pGAP promoter, though understood to be a constitutive (such as non-inducible by feeding with specific carbon sources) promoter, is a metabolic promoter that exerts increasing promoter strength with increasing growth rate. Therefore, the pGAP promoter is hardly suitable in an efficient production process during the cultivation of the host cell line in phases that are characterized by a low growth rate.

In contrast, the promoter of the invention surprisingly maintains its high promoter strength (essentially) at a constantly high transcript level at all growth phases of a host cell culture.

The native pGAP promoter specifically is active in a recombinant eukaryotic cell in a similar way as in a native eukaryotic cell of the same species or strain, including the unmodified (non-recombinant) or recombinant eukaryotic cell. Such native pGAP promoter is commonly understood to be an endogenous promoter, thus, homologous to the eukaryotic cell, and serves as a standard or reference promoter for comparison purposes.

For example, a native pGAP promoter of *P. pastoris* is the unmodified, endogenous promoter sequence in *P. pastoris*, as used to control the expression of GAPDH in *P. pastoris*, e.g. having the sequence shown in FIG. 3: native pGAP promoter sequence of *P. pastoris* (GS115) (SEQ ID 13). If *P. pastoris* is used as a host for producing a POI according to the invention, the transcription strength or rate of the promoter according to the invention is compared to such native pGAP promoter of *P. pastoris*.

As another example, a native pGAP promoter of *S. cerevisiae* is the unmodified, endogenous promoter sequence in *S. cerevisiae*, as used to control the expression of GAPDH in *S. cerevisiae*. If *S. cerevisiae* is used as a host for producing a POI according to the invention, the transcription strength or rate of the promoter according to the invention is compared to such native pGAP promoter of *S. cerevisiae*.

Therefore, the relative expression or transcription strength of a promoter according to the invention is usually compared to the native pGAP promoter of a cell of the same species or strain that is used as a host for producing a POI.

It is specifically understood that the promoter of the invention is preferably not a metabolic promoter such as for example a promoter naturally operably linked to a gene encoding an abundant glycolytic enzyme or an enzyme of gluconeogenesis, a ribosomal protein or an enzyme such as an intracellular protease or a protease being secreted from the host cell.

Specifically preferred is a promoter of the invention, which has at least an expression strength or transcription strength of pCS1. The comparative promoter strength employing the pGAP promoter as a reference may be determined by standard means, such as by measuring the quantity of expression products or the quantity of transcripts, e.g. employing a microarray, Northern Blot, RNA sequencing or qRT-PCR, or else in a cell culture, such as by measuring the quantity of respective gene expression products in recombinant cells. Exemplary tests are illustrated in the Examples section.

The term "protein of interest (POI)" as used herein refers to a polypeptide or a protein that is produced by means of recombinant technology in a host cell. More specifically, the protein may either be a polypeptide not naturally occurring in the host cell, i.e. a heterologous protein, or else may be native to the host cell, i.e. a homologous protein to the host cell, but is produced, for example, by transformation with a self-replicating vector containing the nucleic acid sequence encoding the POI, or upon integration by recombinant techniques of one or more copies of the nucleic acid sequence encoding the POI into the genome of the host cell, or by recombinant modification of one or more regulatory sequences controlling the expression of the gene encoding the POI, e.g. of the promoter sequence. In some cases the term POI as used herein also refers to any metabolite product by the host cell as mediated by the recombinantly expressed protein.

According to a specific embodiment, the term POI would exclude the CS1 protein of *Pichia pastoris*, e.g. characterized by any of the amino acid sequences of FIG. 2, in particular, if the promoter of the invention is natively associated with any of the nucleic acid sequences encoding such CS1 protein.

Specifically, the POI as described herein is a eukaryotic protein, preferably a mammalian protein, specifically a protein heterologous to the host cell.

A POI produced according to the invention may be a multimeric protein, preferably a dimer or tetramer.

According to one aspect of the invention, the POI is a recombinant or heterologous protein, preferably selected from therapeutic proteins, including antibodies or fragments thereof, enzymes and peptides, protein antibiotics, toxin fusion proteins, carbohydrate-protein conjugates, structural proteins, regulatory proteins, vaccines and vaccine like proteins or particles, process enzymes, growth factors, hormones and cytokines, or a metabolite of a POI.

A specific POI is an antigen binding molecule such as an antibody, or a fragment thereof. Among specific POIs are antibodies such as monoclonal antibodies (mAbs), immunoglobulin (Ig) or immunoglobulin class G (IgG), heavy-chain antibodies (HcAb's), or fragments thereof such as fragment-antigen binding (Fab), Fd, single-chain variable fragment (scFv), or engineered variants thereof such as for example Fv dimers (diabodies), Fv trimers (triabodies), Fv tetramers, or minibodies and single-domain antibodies like VH or VHH or V-NAR.

According to a specific embodiment, a fermentation product is manufactured using the POI, a metabolite or a derivative thereof.

The POI may specifically be recovered from the cell culture in the purified form, e.g. substantially pure.

The term "substantially pure" or "purified" as used herein shall refer to a preparation comprising at least 50% (w/w), preferably at least 60%, 70%, 80%, 90% or 95% of a compound, such as a nucleic acid molecule or a POI. Purity is measured by methods appropriate for the compound (e.g. chromatographic methods, polyacrylamide gel electrophoresis, HPLC analysis, and the like).

The term "recombinant" as used herein shall mean "being prepared by or the result of genetic engineering". Thus, a "recombinant microorganism" comprises at least one "recombinant nucleic acid". A recombinant microorganism specifically comprises an expression vector or cloning vector, or it has been genetically engineered to contain a recombinant nucleic acid sequence. A "recombinant protein" is produced by expressing a respective recombinant nucleic acid in a host. A "recombinant promoter" is a genetically engineered non-coding nucleotide sequence suitable for its use as a functionally active promoter as described herein.

Therefore, a new promoter was identified with unique functional properties. Unexpectedly, PAS_chr1-4 (herein called CS1 gene, SEQ ID 9) was identified by analysis of transcription strength in production process conditions as the strongest transcribed gene in *P. pastoris*. The encoded CS1 protein (SEQ ID 10) is not a glycolytic enzyme or protein, but predicted to be located on the cell surface via a GPI-anchor. Though the 9.43 Mbp genomic sequence of the GS115 strain of *P. pastoris* has been determined and disclosed in US20110021378A1, the properties of individual sequences, such as promoter sequences, have not been investigated in detail.

It was surprising that such promoter could be effectively used according to the invention. *Pichia* promoters of the prior art such as used in industrial scale POI production were mainly derived from the methanol metabolic pathway and needed the addition of methanol to induce POI production, which is often not desired. The promoter and method according to the invention has the advantage that it may provide for an increased production by an enhanced expression, and has the reduced risk of contamination due to the specific promoter regulation, in particular when using a chemically defined medium, free of methanol.

It turned out that the promoter according to the invention would exert its improved activity mainly independent of a suitable carbon substrate amount and specific culture media. As an example, *P. pastoris* could be successfully cultivated under conditions of an industrial production process. First a batch culture on a basal carbon source, such as glycerol, was employed, followed by a fed batch with limited feed of a supplemental carbon source, such as glucose. Samples were taken close to the end of the first batch phase, and in limited growth conditions, e.g. using a limited amount of supplemental carbon source. Transcriptome analysis with DNA microarrays revealed specific genes that are strongly active on the supplemental carbon source and in the presence of surplus carbon, i.e. the basal carbon source in excess amount. The pCS1 promoter sequence was identified as surprisingly strong promoter at high and low growth rates. The comparable pGAP promoter of the prior art was significantly weaker.

The features of strong recombinant gene expression on the basal carbon source, and strong expression on limited supplemental carbon source, could be verified in fermentation processes.

The nucleotide sequences that could be used as constitutive promoter sequences according to the invention, would provide for an improved recombinant protein production, can be obtained from a variety of sources. The origin of the promoter according to the invention is preferably from a yeast cell, most preferably from methylotrophic yeast such as from the *Pichia* genus or from the *P. pastoris* species, which promoter may then be used as a parent sequence to produce suitable variants, e.g. mutants or analogs.

It is contemplated that a series of yeast cells, in particular of *Pichia* strains, may be suitable to obtain respective promoter sequences or respective analogs in different species.

Variants of the identified *P. pastoris* promoter, including functionally active variants, such as homologs and analogs may be produced employing standard techniques. The promoter may e.g. be modified to generate promoter variants with altered expression levels and regulatory properties.

For instance, a promoter library may be prepared by mutagenesis of the promoter sequences according to the invention, which may be used as parent molecules, e.g. to fine-tune the gene expression in eukaryotic cells by analysing variants for their expression under different fermentation strategies and selecting suitable variants. A synthetic library of variants may be used, e.g. to select a promoter matching the requirements for producing a selected POI. Such variants may have increased expression efficiency in eukaryotic host cells and high expression under carbon source rich and limiting conditions.

The differential fermentation strategies would distinguish between a growth phase and a production phase. Growth and/or production can suitably take place in batch mode, fed-batch mode or continuous mode. Any suitable bioreactor can be used, including batch, fed-batch, continuous, stirred tank reactor, or airlift reactor.

It is advantageous to provide for the fermentation process on a pilot or industrial scale. The industrial process scale would preferably employ volumina of at least 10 L, specifically at least 50 L, preferably at least 1 $m^3$, preferably at least 10 $m^3$, most preferably at least 100 $m^3$.

Production conditions in industrial scale are preferred, which refer to e.g. fed batch cultivation in reactor volumes of 100 L to 10 $m^3$ or larger, employing typical process times of several days, or continuous processes in fermenter volumes of approximately 50-1000 L or larger, with dilution rates of approximately 0.02-0.15 $h^{-1}$.

The suitable cultivation techniques may encompass cultivation in a bioreactor starting with a batch phase, followed by a short exponential fed batch phase at high specific growth rate, further followed by a fed batch phase at a low specific growth rate. Another suitable cultivation technique may encompass a batch phase followed by a continuous cultivation phase at a low dilution rate.

A preferred embodiment of the invention includes a batch culture to provide biomass followed by a fed-batch culture for high yields POI production.

It is preferred to cultivate the host cell line according to the invention in a bioreactor under growth conditions to obtain a cell density of at least 1 g/L cell dry weight, more preferably at least 10 g/L cell dry weight, preferably at least 20 g/L cell dry weight. It is advantageous to provide for such yields of biomass production on a pilot or industrial scale.

A growth medium allowing the accumulation of biomass, specifically a basal growth medium, typically comprises a carbon source, a nitrogen source, a source for sulphur and a source for phosphate. Typically, such a medium comprises furthermore trace elements and vitamins, and may further comprise amino acids, peptone or yeast extract.

Preferred nitrogen sources include $NH_4H_2PO_4$, or $NH_3$ or $(NH4)_2SO_4$;

Preferred sulphur sources include $MgSO_4$, or $(NH4)_2SO_4$ or $K_2SO_4$;

Preferred phosphate sources include $NH_4H_2PO_4$, or $H_3PO_4$ or $NaH_2PO_4$, $KH_2PO_4$, $Na_2HPO_4$ or $K_2HPO_4$;

Further typical medium components include KCl, $CaCl_2$, and Trace elements such as: Fe, Co, Cu, Ni, Zn, Mo, Mn, I, B;

Preferably the medium is supplemented with vitamin $B_7$;

A typical growth medium for *P. pastoris* comprises glycerol, sorbitol or glucose, $NH_4H_2PO_4$, $MgSO_4$, KCl, $CaCl_2$, biotin, and trace elements.

In the production phase a production medium is specifically used with only a limited amount of a supplemental carbon source.

Preferably the host cell line is cultivated in a mineral medium with a suitable carbon source, thereby further simplifying the isolation process significantly. An example of a preferred mineral medium is one containing an utilizable carbon source (e.g. glucose, glycerol, sorbitol or methanol), salts containing the macro elements (potassium, magnesium, calcium, ammonium, chloride, sulphate, phosphate) and trace elements (copper, iodide, manganese, molybdate, cobalt, zinc, and iron salts, and boric acid), and optionally vitamins or amino acids, e.g. to complement auxotrophies.

The cells are cultivated under conditions suitable to effect expression of the desired POI, which can be purified from the cells or culture medium, depending on the nature of the expression system and the expressed protein, e.g. whether the protein is fused to a signal peptide and whether the protein is soluble or membrane-bound. As will be understood by the skilled artisan, cultivation conditions will vary according to factors that include the type of host cell and particular expression vector employed.

By selecting the suitable promoter sequence according to the invention, optionally in combination with further preferred regulatory sequences, it is possible to provide for, under comparable conditions, at least the same, or at least about an 1.1-fold, or at least about 1.2-fold, at least about 1.5-fold, at least about 2-fold, at least about 3-fold, at least about 4-fold, at least about 5-fold, at least about 10-fold, or at least up to about a 15-fold activity, e.g. under growth-limited conditions in a fed-batch process, as represented by the promoter activity or transcription strength, or regulated by the promoter strength relative to a GAP promoter that is homologous to the production cell, a native pGAP, or isolated from *P. pastoris*.

A typical production medium comprises a supplemental carbon source, and further $NH_4H_2PO_4$, $MgSO_4$, KCl, $CaCl_2$, biotin, and trace elements.

For example the feed of the supplemental carbon source added to the fermentation may comprise a carbon source with up to 50 wt % utilizable sugars. The low feed rate of the supplemental medium will limit the effects of product or byproduct inhibition on the cell growth, thus a high product yield based on substrate provision will be possible.

The fermentation preferably is carried out at a pH ranging from 3 to 7.5.

Typical fermentation times are about 24 to 120 hours with temperatures in the range of 20° C. to 35° C., preferably 22-30° C.

In general, the recombinant nucleic acids or organisms as referred to herein may be produced by recombination techniques well known to a person skilled in the art. In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual, Cold Spring Harbor, (1982).

According to a preferred embodiment of the present invention, a recombinant construct is obtained by ligating the promoter and relevant genes into a vector or expression construct. These genes can be stably integrated into the host cell genome by transforming the host cell using such vectors or expression constructs.

Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector.

Appropriate expression vectors typically comprise further regulatory sequences suitable for expressing DNA encoding a POI in a eukaryotic host cell. Examples of regulatory sequences include operators, enhancers, ribosomal binding sites, and sequences that control transcription and translation initiation and termination. The regulatory sequences may be operably linked to the DNA sequence to be expressed.

To allow expression of a recombinant nucleotide sequence in a host cell, the expression vector may provide the promoter according to the invention adjacent to the 5' end of the coding sequence, e.g. upstream from the GOI or a signal peptide gene enabling secretion of the POI. The transcription is thereby regulated and initiated by this promoter sequence.

A signal peptide may be a heterologous signal peptide or a hybrid of a native and a heterologous signal peptide, and may specifically be heterologous or homologous to the host organism producing the protein. The function of the signal peptide is to allow the POI to be secreted to enter the endoplasmatic reticulum. It is usually a short (3-60 amino acids long) peptide chain that directs the transport of a protein outside the plasma membrane, thereby making it easy to separate and purify the heterologous protein. Some signal peptides are cleaved from the protein by signal peptidase after the proteins are transported.

Exemplary signal peptides are signal sequences from *S. cerevisiae* alpha-mating factor prepro peptide and the signal peptide from the *P. pastoris* acid phosphatase gene (PHO1).

A promoter sequence is understood to be operably linked to a coding sequence, if the promoter controls the transcription of the coding sequence. If a promoter sequence is not natively associated with the coding sequence, its transcription is either not controlled by the promoter in native (wild-type) cells or the sequences are recombined with different contiguous sequences.

To prove the function of the relevant sequences, expression vectors comprising one or more of the regulatory elements may be constructed to drive expression of a POI, and the expressed yield is compared to constructs with conventional regulatory elements. A detailed description of the experimental procedure can be found in the examples below. The identified genes may be amplified by PCR from *P. pastoris* using specific nucleotide primers, cloned into an expression vector and transformed into a eukaryotic cell line, e.g. using a yeast vector and a strain of *P. pastoris*, for high level production of various different POI. To estimate the effect of the promoter according to the invention on the amount of recombinant POI so produced, the eukaryotic cell line may be cultured in shake flask experiments and fedbatch or chemostat fermentations in comparison with strains comprising a conventional constitutive, e.g. a growth-dependent promoter, such as for example the standard pGAP promoter in the respective cell. In particular, the choice of the promoter has a great impact on the recombinant protein production.

The POI can be produced using the recombinant host cell line by culturing a transformant, thus obtained in an appropriate medium, isolating the expressed product or metabolite from the culture, and optionally purifying it by a suitable method.

Transformants according to the present invention can be obtained by introducing such a vector DNA, e.g. plasmid DNA, into a host and selecting transformants which express the POI or the host cell metabolite with high yields. Host cells are treated to enable them to incorporate foreign DNA by methods conventionally used for transformation of eukaryotic cells, such as the electric pulse method, the protoplast method, the lithium acetate method, and modified methods thereof. *P. pastoris* is preferably transformed by electroporation. Preferred methods of transformation for the uptake of the recombinant DNA fragment by the microorganism include chemical transformation, electroporation or transformation by protoplastation. Transformants according to the present invention can be obtained by introducing such a vector DNA, e.g. plasmid DNA, into a host and selecting transformants which express the relevant protein or host cell metabolite with high yields.

Several different approaches for the production of the POI according to the method of the invention are preferred. Substances may be expressed, processed and optionally secreted by transforming a eukaryotic host cell with an expression vector harbouring recombinant DNA encoding a relevant protein and at least one of the regulatory elements as described above, preparing a culture of the transformed cell, growing the culture, inducing transcription and POI production, and recovering the product of the fermentation process.

The host cell according to the invention is preferably tested for its expression capacity or yield by the following test: ELISA, activity assay, HPLC, or other suitable tests.

The POI is preferably expressed employing conditions to produce yields of at least 1 mg/L, preferably at least 10 mg/L, preferably at least 100 mg/L, most preferred at least 1 g/L.

It is understood that the methods disclosed herein may further include cultivating said recombinant host cells under conditions permitting the expression of the POI, preferably in the secreted form or else as intracellular product. A recombinantly produced POI or a host cell metabolite can then be isolated from the cell culture medium and further purified by techniques well known to a person skilled in the art.

The POI produced according to the invention typically can be isolated and purified using state of the art techniques, including the increase of the concentration of the desired POI and/or the decrease of the concentration of at least one impurity.

If the POI is secreted from the cells, it can be isolated and purified from the culture medium using state of the art techniques. Secretion of the recombinant expression products from the host cells is generally advantageous for reasons that include facilitating the purification process, since the products are recovered from the culture supernatant rather than from the complex mixture of proteins that results when yeast cells are disrupted to release intracellular proteins.

The cultured transformant cells may also be ruptured sonically or mechanically, enzymatically or chemically to obtain a cell extract containing the desired POI, from which the POI is isolated and purified.

As isolation and purification methods for obtaining a recombinant polypeptide or protein product, methods, such as methods utilizing difference in solubility, such as salting out and solvent precipitation, methods utilizing difference in molecular weight, such as ultrafiltration and gel electrophoresis, methods utilizing difference in electric charge, such as ion-exchange chromatography, methods utilizing specific affinity, such as affinity chromatography, methods utilizing difference in hydrophobicity, such as reverse phase high performance liquid chromatography, and methods utilizing difference in isoelectric point, such as isoelectric focusing may be used.

The highly purified product is essentially free from contaminating proteins, and preferably has a purity of at least 90%, more preferred at least 95%, or even at least 98%, up to 100%. The purified products may be obtained by purification of the cell culture supernatant or else from cellular debris.

As isolation and purification methods the following standard methods are preferred: Cell disruption (if the POI is obtained intracellularly), cell (debris) separation and wash by Microfiltration or Tangential Flow Filter (TFF) or centrifugation, POI purification by precipitation or heat treatment, POI activation by enzymatic digest, POI purification by chromatography, such as ion exchange (IEX), hydrophobic interaction chromatography (HIC), Affinity chromatography, size exclusion (SEC) or HPLC Chromatography, POI precipitation of concentration and washing by ultrafiltration steps.

The isolated and purified POI can be identified by conventional methods such as Western blot, HPLC, activity assay, or ELISA.

The POI can be any eukaryotic, prokaryotic or synthetic polypeptide. It can be a secreted protein or an intracellular protein. The present invention also provides for the recombinant production of functional homologs, functional equivalent variants, derivatives and biologically active fragments of naturally occurring proteins. Functional homologs are preferably identical with or correspond to and have the functional characteristics of a sequence.

A POI referred to herein may be a product homologous to the eukaryotic host cell or heterologous, preferably for therapeutic, prophylactic, diagnostic, analytic or industrial use.

The POI is preferably a heterologous recombinant polypeptide or protein, produced in a eukaryotic cell, preferably a yeast cell, preferably as secreted proteins. Examples of preferably produced proteins are immunoglobulins, immunoglobulin fragments, aprotinin, tissue factor pathway inhibitor or other protease inhibitors, and insulin or insulin precursors, insulin analogues, growth hormones, interleukins, tissue plasminogen activator, transforming growth factor a or b, glucagon, glucagon-like peptide 1 (GLP-1), glucagon-like peptide 2 (GLP-2), GRPP, Factor VII, Factor VIII, Factor XIII, platelet-derived growth factor1, serum albumin, enzymes, such as lipases or proteases, or a functional homolog, functional equivalent variant, derivative and biologically active fragment with a similar function as the native protein. The POI may be structurally similar to the native protein and may be derived from the native protein by addition of one or more amino acids to either or both the C- and N-terminal end or the side-chain of the native protein, substitution of one or more amino acids at one or a number of different sites in the native amino acid sequence, deletion of one or more amino acids at either or both ends of the native protein or at one or several sites in the amino acid sequence, or insertion of one or more amino acids at one or more sites in the native amino acid sequence. Such modifications are well known for several of the proteins mentioned above.

A POI can also be selected from substrates, enzymes, inhibitors or cofactors that provide for biochemical reactions in the host cell, with the aim to obtain the product of said biochemical reaction or a cascade of several reactions, e.g. to obtain a metabolite of the host cell. Exemplary products can be vitamins, such as riboflavin, organic acids, and alcohols, which can be obtained with increased yields following the expression of a recombinant protein or a POI according to the invention.

In general, the host cell, which expresses a recombinant product, can be any eukaryotic cell suitable for recombinant expression of a POI.

Examples of preferred mammalian cells are BHK, CHO (CHO-DG44, CHO-DUXB11, CHO-DUKX, CHO-K1, CHOK1SV, CHO-S), HeLa, HEK293, MDCK, NIH3T3, NS0, PER.C6, SP2/0 and VERO cells.

Examples of preferred yeast cells used as host cells according to the invention include but are not limited to the *Saccharomyces* genus (e.g. *Saccharomyces cerevisiae*), the *Pichia* genus (e.g. *P. pastoris*, or *P. methanolica*), the *Komagataella* genus (*K. pastoris, K. pseudopastoris* or *K. phaffii*), *Hansenula polymorpha* or *Kluyveromyces lactis*.

Newer literature divides and renames *Pichia pastoris* into *Komagataella pastoris, Komagataella phaffii* and *Komagataella pseudopastoris*. Herein *Pichia pastoris* is used synonymously for all, *Komagataella pastoris, Komagataella phaffii* and *Komagataella pseudopastoris*.

The preferred yeast host cells are derived from methylotrophic yeast, such as from *Pichia* or *Komagataella*, e.g. *Pichia pastoris*, or *Komagataella pastoris*, or *K. phaffii*, or *K. pseudopastoris*. Examples of the host include yeasts such as *P. pastoris*. Examples of *P. pastoris* strains include CBS 704 (=NRRL Y-1603=DSMZ 70382), CBS 2612 (=NRRL Y-7556), CBS 7435 (=NRRL Y-11430), CBS 9173-9189 (CBS strains: CBS-KNAW Fungal Biodiversity Centre, Centraalbureau voor Schimmelcultures, Utrecht, The Netherlands), and DSMZ 70877 (German Collection of Microorganisms and Cell Cultures), but also strains from Invitrogen, such as X-33, GS115, KM71 and SMD1168. Examples of *S. cerevisiae* strains include W303, CEN.PK and the BY-series (EUROSCARF collection). All of the strains described above have been successfully used to produce transformants and express heterologous genes.

A preferred yeast host cell according to the invention, such as a *P. pastoris* or *S. cerevisiae* host cell, contains a heterologous or recombinant promoter sequences, which may be derived from a *P. pastoris* or *S. cerevisiae* strain, different from the production host. In another specific embodiment the host cell according to the invention comprises a recombinant expression construct according to the invention comprising the promoter originating from the same genus, species or strain as the host cell.

The promoter of the invention is preferably derived from a gene encoding a protein homologous to the host cell.

For example, a promoter according to the invention may be derived from yeast, such as a *S. cerevisiae* strain, and be used to express a POI in a yeast. A specifically preferred embodiment relates to a promoter according to the invention originating from *P. pastoris* for use in a method to produce a recombinant POI in a *P. pastoris* producer host cell line. The homologous origin of the nucleotide sequence facilitates its incorporation into the host cell of the same genus or species, thus enabling stable production of a POI, possibly with increased yields in industrial manufacturing processes. Also, functionally active variants of the promoter from other suitable yeasts or other fungi or from other organisms such as vertebrates or plants can be used.

If the POI is a protein homologous to the host cell, i.e. a protein which is naturally occurring in the host cell, the expression of the POI in the host cell may be modulated by the exchange of its native promoter sequence with a promoter sequence according to the invention.

This purpose may be achieved e.g. by transformation of a host cell with a recombinant DNA molecule comprising homologous sequences of the target gene to allow site specific recombination, the promoter sequence and a selective marker suitable for the host cell. The site specific recombination shall take place in order to operably link the promoter sequence with the nucleotide sequence encoding the POI. This results in the expression of the POI from the promoter sequence according to the invention instead of from the native promoter sequence.

In a specifically preferred embodiment of the invention the promoter sequence has an increased promoter activity relative to the native promoter sequence of the POI.

According to the invention it is preferred to provide a *P. pastoris* host cell line comprising a promoter sequence according to the invention operably linked to the nucleotide sequence coding for the POI.

According to the invention it is also possible to provide a wildcard vector or host cell according to the invention, which comprises a promoter according to the invention, and which is ready to incorporate a gene of interest encoding a POI. The wildcard cell line is, thus, a preformed host cell line, which is characterized for its expression capacity. This follows an innovative "wildcard" platform strategy for the generation of producer cell lines, for the POI production, e.g. using site-specific recombinase-mediated cassette exchange. Such a new host cell facilitates the cloning of a gene of interest (GOI), e.g. into predetermined genomic expression hot spots within days in order to get reproducible, highly efficient production cell lines.

According to a preferred embodiment the method according to the invention employs a recombinant nucleotide sequence encoding the POI, which is provided on a plasmid suitable for integration into the genome of the host cell, in a single copy or in multiple copies per cell. The recombinant nucleotide sequence encoding the POI may also be provided on an autonomously replicating plasmid in a single copy or in multiple copies per cell.

The preferred method according to the invention employs a plasmid, which is a eukaryotic expression vector, preferably a yeast expression vector. Expression vectors may include but are not limited to cloning vectors, modified cloning vectors and specifically designed plasmids. The preferred expression vector as used in the invention may be any expression vector suitable for expression of a recombinant gene in a host cell and is selected depending on the host organism. The recombinant expression vector may be any vector which is capable of replicating in or integrating into the genome of the host organisms, also called host vector, such as a yeast vector, which carries a DNA construct according to the invention. A preferred yeast expression vector is for expression in yeast selected from the group consisting of methylotrophic yeasts represented by the genera *Hansenula, Pichia, Candida* and *Torulopsis*.

In the present invention, it is preferred to use plasmids derived from pPICZ, pGAPZ, pPIC9, pPICZalfa, pGAPZalfa, pPIC9K, pGAPHis or pPUZZLE as the vector.

According to a preferred embodiment of the present invention, a recombinant construct is obtained by ligating the relevant genes into a vector. These genes can be stably integrated into the host cell genome by transforming the host cell using such vectors. The polypeptides encoded by the genes can be produced using the recombinant host cell line by culturing a transformant, thus obtained in an appropriate medium, isolating the expressed POI from the culture, and purifying it by a method appropriate for the expressed product, in particular to separate the POI from contaminating proteins.

Expression vectors may comprise one or more phenotypic selectable markers, e.g. a gene encoding a protein that confers antibiotic resistance or that supplies an autotrophic requirement. Yeast vectors commonly contain an origin of replication from a yeast plasmid, an autonomously replicating sequence (ARS), or alternatively, a sequence used for integration into the host genome, a promoter region, sequences for polyadenylation, sequences for transcription termination, and a selectable marker.

The procedures used to ligate the DNA sequences, e.g. coding for the precursing sequence and/or the POI, the promoter and the terminator, respectively, and to insert them into suitable vectors containing the information necessary for integration or host replication, are well known to persons skilled in the art, e.g. described by J. Sambrook et al., (A Laboratory Manual, Cold Spring Harbor, 1989).

It will be understood that the vector, which uses the regulatory elements according to the invention and/or the POI as an integration target, may be constructed either by first preparing a DNA construct containing the entire DNA sequence coding for the regulatory elements and/or the POI and subsequently inserting this fragment into a suitable expression vector, or by sequentially inserting DNA fragments containing genetic information for the individual elements, followed by ligation.

Also multicloning vectors, which are vectors having a multicloning site, can be used according to the invention, wherein a desired heterologous gene can be incorporated at a multicloning site to provide an expression vector. In expression vectors, the promoter is placed upstream of the gene of the POI and regulates the expression of the gene. In the case of multicloning vectors, because the gene of the POI is introduced at the multicloning site, the promoter is placed upstream of the multicloning site.

The DNA construct as provided to obtain a recombinant host cell according to the invention may be prepared synthetically by established standard methods, e.g. the phosphoramidite method. The DNA construct may also be of genomic or cDNA origin, for instance obtained by preparing a genomic or cDNA library and screening for DNA sequences coding for all or part of the polypeptide of the invention by hybridization using synthetic oligonucleotide probes in accordance with standard techniques (Sambrook et al., Molecular Cloning: A Laboratory Manual, Cold Spring Harbor, 1989). Finally, the DNA construct may be of mixed synthetic and genomic, mixed synthetic and cDNA or mixed genomic and cDNA origin prepared by annealing fragments of synthetic, genomic or cDNA origin, as appropriate, the fragments corresponding to various parts of the entire DNA construct, in accordance with standard techniques.

In another preferred embodiment, the yeast expression vector is able to stably integrate in the yeast genome, e. g. by homologous recombination.

A transformant host cell according to the invention obtained by transforming the cell with the regulatory elements according to the invention and/or the POI genes may preferably first be cultivated at conditions to grow efficiently to a large cell number. When the cell line is prepared for the POI expression, cultivation techniques are chosen to produce the expression product.

Specific examples relate to fed-batch fermentation of a recombinant production *P. pastoris* cell line producing reporter proteins, employing a glycerol batch medium and a glucose fed batch medium. Comparative promoter activity studies have proven that the promoter according to the invention may be successfully used for recombinant protein production.

According to a further example, human serum albumin (HSA) was produced as a POI under the glucose-limit conditions, and the HSA yield and gene copy number determined.

According to another example, fed-batch cultivation of *P. pastoris* strains expressing HSA under the control of a promoter according to the invention was performed.

Further examples refer to expressing a porcine carboxypeptidase B as model protein under transcriptional control of the pCS1 promoter.

Yet, a further example refers to the expression of an antibody fragment under the transcriptional control of pCS1.

A further example refers to size or length variants of a promoter according to the invention, such as the elongated pCS1 sequence pCS1a (SEQ ID 2) which comprises the pCS1 sequence and an elongation at the 5' end, or fragments of pCS1 with a length in the range of about 80 bp to 800 bp.

The foregoing description will be more fully understood with reference to the following examples. Such examples are, however, merely representative of methods of practicing one or more embodiments of the present invention and should not be read as limiting the scope of invention.

EXAMPLES

Examples below illustrate the materials and methods used to identify a new promoter and to analyze its expression properties in *Pichia pastoris*.

Example 1: Identification of a Strongly Expressed Gene in *P. pastoris*

In order to identify a strong gene and its respective promoter of *P. pastoris*, analysis of gene expression patterns was done using DNA microarrays. *P. pastoris* cells grown in a glycerol batch and in glucose limit (chemostat) were analyzed.

a) Strain

A wild type *P. pastoris* strain (CBS2612, CBS-KNAW Fungal Biodiversity Centre, Centraalbureau voor Schimmelcultures, Utrecht, The Netherlands), which can grow on minimal media without supplements, was used.

b) Cultivation of *P. pastoris*

Fermentations were performed with Minifors reactors (Infors-HT, Switzerland) with a final working volume of 2.5 L.

Following media were used:

PTM$_1$ Trace Salts Stock Solution Contained Per Liter 6.0 g CuSO$_4$.5H$_2$O, 0.08 g NaI, 3.36 g MnSO$_4$.H$_2$O, 0.2 g Na$_2$MoO$_4$.2H$_2$O, 0.02 g H$_3$BO$_3$, 0.82 g CoCl$_2$, 20.0 g ZnCl$_2$, 65.0 g FeSO$_4$.7H$_2$O, 0.2 g biotin and 5.0 ml H$_2$SO$_4$ (95%-98%).

Glycerol Batch Medium Contained Per Liter 2 g Citric acid monohydrate (C$_6$H$_8$O$_7$.H$_2$O), 39.2 g Glycerol, 20.8 g NH$_4$H$_2$PO$_4$, 0.5 g MgSO$_4$.7H$_2$O, 1.6 g KCl, 0.022 g CaCl$_2$.2H$_2$O, 0.8 mg biotin and 4.6 ml PTM1 trace salts stock solution. HCl was added to set the pH to 5.

Glycerol Fed-Batch Medium Contained Per Liter 632 g glycerol, 8 g MgSO$_4$.7H$_2$O, 22 g KCl, and 0.058 g CaCl$_2$.2H$_2$O.

Chemostat Medium Contained Per Liter 2 g Citric acid monohydrate (C$_6$H$_8$O$_7$.H$_2$O), 99.42 g glucose monohydrate, 22 g NH$_4$H$_2$PO$_4$, 1.3 g MgSO$_4$.7H$_2$O, 3.4 g KCl, 0.02 g CaCl$_2$.2H$_2$O, 0.4 mg biotin and 3.2 ml PTM1 trace salts stock solution. HCl was added to set the pH to 5.

The dissolved oxygen was controlled at DO=20% with the stirrer speed (500-1250 rpm). Aeration rate was 60 L h$^{-1}$ air, the temperature was controlled at 25° C. and the pH setpoint of 5 was controlled with addition of NH$_4$OH (25%).

To start the fermentation, 1.5 L batch medium was sterile filtered into the fermenter and *P. pastoris* was inoculated (from an overnight pre-culture in YPG, 180 rpm, 28° C.) with a starting optical density (OD600) of 1. The batch phase of approximately 25 h reached a dry biomass concentration of approximately 20 g/L, it was followed by a 10 h exponential fed batch with glucose medium, leading to a dry biomass concentration of approximately 50 g/L. Then, the volume was reduced to 1.5 L and the chemostat cultivation was started with a feed/harvest rate of 0.15 L h$^{-1}$, resulting in a constant growth rate of µ=0.1. The fermentation was terminated 50 h after the chemostat start.

This fermentation has been performed three times to obtain the biological replicates necessary for reliable microarray analysis.

Carbon limited conditions (no detectable residual glucose) during the chemostat were verified by HPLC analysis of the culture supernatant.

c) Sampling

Samples were taken at the end of the glycerol batch phase and in steady state conditions of the glucose chemostat. Routine sampling as determination of optical density or yeast dry mass, qualitative microscopic inspection and cell viability analysis was done alongside during each fermentation. For microarray analysis, samples were taken and treated as follows: For optimal quenching, 9 mL cell culture broth was immediately mixed with 4.5 mL of ice cold 5% phenol (Sigma) solution (in Ethanol abs.), and aliquoted. Each 2 mL were centrifuged (13200 rpm for 1 minute) in pre-cooled collection tubes (GE healthcare, NJ), supernatant was removed completely and the tubes were stored at −80° C. until RNA purification.

d) RNA Purification and Sample Preparation for Microarray Hybridization

The RNA was isolated using TRI reagent according to the suppliers instructions (Ambion, US). The cell pellets were resuspended in TRI reagent and homogenized with glass beads using a FastPrep 24 (M.P. Biomedicals, CA) at 5 m s$^{-1}$ for 40 seconds. After addition of chloroform, the samples were centrifuged and the total RNA was precipitated from the aqueous phase by adding isopropanol. The pellet was washed with 70% ethanol, dried and re-suspended in RNAse free water. RNA concentrations were determined by measuring OD260 using a Nanodrop 1000 spectrophotometer (NanoDrop products, DE). Remaining DNA from the samples was removed using the DNA free Kit (Ambion, CA). Sample volume equal to 10 µg RNA was diluted to 50 µL in RNAse free water, then DNAse buffer I and rDNAse I were added and incubated at 37° C. for 30 minutes. After addition of DNAse Inactivation Reagent, the sample was centrifuged and the supernatant was transferred into a fresh tube. RNA concentrations were determined again as described above. Additionally, RNA integrity was analyzed using RNA nano chips (Agilent). To monitor the microarray workflow from amplification and labelling to hybridisation of the samples, the Spike In Kit (Agilent, Product Nr.: 5188-5279) was used as positive control. It contains 10 different polyadenylated transcripts from an adenovirus, which are amplified, labelled and cohybridised together with the own RNA samples. The samples were labelled with Cy 3 and Cy 5 using the Quick Amp Labelling Kit (Agilent, Prod. Nr.: 5190-0444). Therefore 500 ng of purified sample RNA were diluted in 8.3 µL RNAse free water, 2 µL Spike A or B, and 1.2 µL T7 promoter primer were added. The mixture was denatured for 10 minutes at 65° C. and kept on ice for 5 minutes. Then 8.5 µL cDNA mastermix (per sample: 4 µL 5× first strand buffer, 2 µL 0.1 M DTT, 1 µL 10 mM dNTP mix, 1 µL MMLV-RT, 0.5 µL RNAse out) were added, incubated at 40° C. for 2 hours, then transferred to 65° C. for 15 minutes and put on ice for 5 minutes. The transcription mastermix (per sample: 15.3 µL nuclease free water, 20 µL transcription buffer, 6 µL 0.1 M DTT, 6.4 µL 50% PEG, 0.5 µL RNAse Inhibitor, 0.6 µL inorg. phosphatase, 0.8 µL T7 RNA Polymerase, 2.4 µL Cyanin 3 or Cyanin 5) was prepared and added to each tube and incubated at 40° C. for 2 hours. In order to purify the obtained labelled cRNA, the RNeasy Mini Kit (Qiagen, Cat. No. 74104) was used. Samples were stored at −80° C. Quantification of the cRNA concentration and labelling efficiency was done at the Nanodrop spectrophotometer.

e) Microarray Analysis

The Gene Expression Hybridisation Kit (Agilent, Cat. No. 5188-5242) was used for hybridisation of the labelled sample cRNAs. For the preparation of the hybridisation samples each 300 ng cRNA (Cy3 and Cy 5) and 6 µL 10-fold blocking agent were diluted with nuclease free water to a final volume of 24 µL. After addition of 1 µL 25-fold fragmentation buffer, the mixture was incubated at 60° C. for 30 minutes. Then 25 µL GEx Hybridisation Buffer HI-RPM was added to stop the reaction. After centrifugation for one minute with 13,200 rpm, the sample was chilled on ice and used for hybridisation immediately. In-house designed *P. pastoris* specific oligonucleotide arrays (AMAD-ID: 026594, 8×15K custom arrays, Agilent) were used. Microarray hybridisation was done according to the Microarray Hybridisation Chamber User Guide (Agilent G2534A). First, the gasket slide was uncovered and put onto the chamber base, Agilent label facing up. The sample (40 µL per array) was loaded in the middle of each of the eight squares. Then the microarray slide was carefully put onto the gasket slide (Agilent label facing down) and the chamber cover was placed on and fixed with the clamp. Hybridisation was done in the hybridisation oven for 17 hours at 65° C. Before scanning, the microarray chip was washed. Therefore, the chamber was dismantled, and the sandwich slides were detached from each other while submerged in wash buffer 1. The microarray was directly transferred into another dish with wash buffer 1, washed for 1 minute, transferred into wash buffer 2 (temperature at least 30° C.) and washed for another minute. After drying of the microarray slide by touching the slide edge with a tissue, it was put into the slide holder (Agilent label facing up). The slide holder was put into the carousel and scanning was started.

f) Data Acquisition and Statistical Evaluation of Microarray Data

Images were scanned at a resolution of 50 nm with a G2565AA Microarray scanner (Agilent) and were imported into the Agilent Feature Extraction 9.5 software. Agilent Feature Extraction 9.5 was used for the quantification of the spot intensities. The raw mean spot intensity data was then imported into the open source software R for further normalisation and data analysis.

For data preprocessing and normalization the R packages limma, vsn and marray were used. The intensity data was not background corrected and was normalized with VSN.

The microarray data was browsed for entries with high signal intensity in both states in order to identify strongly expressed constitutive genes. The most strongly transcribed gene is shown in Table 1, with the signal intensity in both states. The data of pGAP and pTEF are added as references. In average, pCS1 exceeded pGAP in both conditions (glycerol batch and glucose-limited chemostat cultivation) by roughly 30%, while pTEF is about 12% weaker than pGAP.

Pre-culture for 24 hours was done with rich medium containing glycerol as carbon source—simulating the batch phase of the process, which was followed by the main culture with minimal medium and glucose feed beads—simulating the glucose-limited fed batch phase of the process. Green fluorescence protein (eGFP) was used as intracellular reporter protein for promoter activity.

a) Strain & Expression Vector

The *P. pastoris* wild type strain (CBS2612, CBS-KNAW Fungal Biodiversity Centre, Centraalbureau voor Schimmelcultures, Utrecht, The Netherlands) was used as host strain. Transformation of the strain was carried out with an in-house vector named pPUZZLE (Stadlmayr et al. J. Biotechnol 2010; 150(4):519-29), comprising of an origin of replication for *E. coli* (pUC19), an antibiotic resistance cassette (Sh ble gene conferring resistance to Zeocin) for selection in *E. coli* and yeast, an expression cassette for the gene of interest (GOI) consisting of a multiple cloning site and the *S. cerevisiae* CYC1 transcription terminator, and a locus for integration into the *P. pastoris* genome (3'AOX1 region).

b) Amplification and Cloning of the Newly Identified Promoter pCS1 into pPUZZLE Expression Vector Containing eGFP as GOI The pCS1 promoter (SEQ ID) comprises 985 bp of the 5'-non coding region of the CS1 gene (see Example 1) up to the start codon ATG and was amplified by PCR (Phusion Polymerase, New England Biolabs) from *P. pastoris* genomic DNA using the primers shown in Table 2. The sequence was cloned into the pPUZZLE expression vector pPM1aZ10_eGFP, cut with ApaI and SbfI, resulting in pPM1aZ10_pCS1_eGFP. Additionally, the vector pPM1aZ10_pGAP_eGFP, containing the commonly used promoter of glyceraldehyde 3-phosphate dehydrogenase promoter (pGAP of *P. pastoris*, here SEQ ID 13) was used as reference. The promoters were inserted upstream of the start codon of the eGFP gene using the ApaI and the SbfI restriction sites (see Tables 2 and 3). The correctness of the promoter sequences was verified by Sanger sequencing.

TABLE 1

Microarray data of the genes, which promoters were selected for further characterization and of pGAP and pTEF as controls

| Promoter | gene identifier | Intensity[1] | % of pGAP intensity/ transcription strength | Intensity[2] | % of pGAP intensity/ transcription strength |
|---|---|---|---|---|---|
| pGAP | PAS_chr2-1_0437 | 56235.2 | 100.0 | 44411.4 | 100.0 |
| pTEF | PAS_FragB_0052 | 47046.3 | 83.4 | 39956.2 | 89.9 |
| pCS1 | PAS_chr1-4_0586 | 83570.4 | 148.6 | 54723.2 | 122.7 |

[1]in glycerol batch phase (average of both channels)
[2]in glucose-limited chemostat (average of both channels)

Example 2: Comparative Promoter Activity Studies of the Newly Identified Promoter pCS1 in *P. pastoris* Using eGFP as Intracellularly Expressed Reporter Gene In order to analyze the properties of the newly identified promoter, shake flask screenings were performed as follows:

TABLE 2

Primers for PCR amplification of the promoters

| Name | Target | Sequence | $T_M$ | Restriction site |
|---|---|---|---|---|
| pCS1_fw | pCS1 | SEQ ID 14 GATAGGGCCCCAGGGCATCATTGAGGTTT CCAC | 69.6 | ApaI |

TABLE 2-continued

Primers for PCR amplification of the promoters

| Name | Target | Sequence | $T_M$ | Restriction site |
|------|--------|----------|-------|------------------|
| pCS1_back | pCS1 | SEQ ID 15 GATACCTGCAGGTTTTGTTGTTGAGTGAAGCGAGTG | 69.3 | SbfI |

TABLE 3

Amplification primers, cloning enzymes and the length of the cloned promoter

| promoter | 5'primer | 3'primer | Cloning enzyme 5' | Cloning enzyme 3' | length |
|----------|----------|----------|-----|-----|--------|
| pCS1 | pCS1_fw | pCS1_back | ApaI | SbfI | 985 | c) Expression of eGFP in *P. pastoris* for Analysis of the Promoter Activity

All plasmids were linearized with AscI within the 3'AOX genome integration region prior to electroporation (2 kV, 4 ms, GenePulser, BioRad) into electrocompetent *P. pastoris*.

Positive transformants were selected on YPD plates (per liter: 10 g yeast extract, 20 g peptone, 20 g glucose, 20 g agar-agar) plates containing 25 μg/mL of Zeocin (Invivogen, CA). Colony PCR was used to ensure the presence of the transformed plasmid. Therefore, genomic DNA was gained by cooking and freezing of *P. pastoris* colonies for 5 minutes each and directly applied for PCR with the appropriate primers. For expression screening, a single colony was inoculated in liquid YPG-Zeo medium (per liter: 20 g peptone, 10 g yeast extract, 12.6 g glycerol and 25 mg Zeocin) as pre-culture. After approximately 24 h the pre-culture was used to inoculate the main culture with an OD600 of 0.1 in 2 mL synthetic screening medium (per liter: 22 g glucose monohydrate, 22 g citric acid, 3.15 g $(NH_4)_2HPO_4$, 0.027 g $CaCl_2 \cdot 2H_2O$, 0.9 g KCl, 0.5 g $MgSO_4 \cdot 7H_2O$, 2 mL 500× biotin and 1.47 mL trace salts stock solution [per liter: 6 g $CuSO_4 \cdot 5H_2O$, 0.08 g NaI, 3 g $MnSO_4 \cdot H_2O$, 0.2 g $Na_2MoO_4 \cdot 2H_2O$, 0.02 g $H_3BO_3$, 0.5 g $CoCl_2$, 20 g $ZnCl_2$, 5 g $FeSO_4 \cdot 7H_2O$ and 5 mL $H_2SO_4$]; pH set to 5 with 5M KOH; sterilized by filtration) and 2 glucose feed bead quarters (second feed bead added after 24 hours; Kuhner, CH). Glucose-limiting growth conditions were achieved due to the slow glucose release kinetics of these feed beads, which is described by the following equation: (Glucose)=1.63*t0.74 [mg/Disc]. Samples were taken at the end of the pre-culture, and 24 and 48 hours after inoculation of the main culture. Cell density was determined by measuring OD600, eGFP expression was analyzed by flow cytometry as described in Stadlmayr et al. (J. Biotechnology 2010 December; 150(4):519-29). For each sample 10,000 cells were analyzed. Auto-fluorescence of *P. pastoris* was measured using untransformed *P. pastoris* wild type cells and subtracted from the signal. Relative eGFP expression levels (fluorescence intensity related to cell size) are shown as percentage of eGFP expression level of a clone expressing eGFP under the control of the constitutive pGAP promoter. The results are shown in Table 4. The clone expressing under the control of the pCS1 promoter exceeded pGAP by 38% at the pre-culture (batch) end, and had 4-fold higher GFP expression levels at the main culture (fed batch) end.

TABLE 4

Average GFP fluorescence per cell size of *P. pastoris* clones expressing eGFP under the control of the novel pCS1 promoter. Data is shown relative to pGAP at the same time point.

| | pre-culture | | main culture | |
|---|---|---|---|---|
| | batch end | stdev | 48 h | stdev |
| pCS1 | 138.2 | 26.6 | 400.7 | 104.87 |
| pGAP | 100.0 | | 100.0 | | d) Determination of eGFP Gene Copy Number (GCN) of the *P. pastoris* Clones of Example 2c GCN stands for the number of reporter protein expression cassettes integrated into the *P. pastoris* genome. GCN determination of clones expressing eGFP under the control of pCS1 or pGAP was done as described in Example 5 further below. eGFP expression levels were analysed as in Example 2c. Exemplarily, the results of one clone of each promoter are shown in Table 5. Clones expressing eGFP under the control of the novel pCS1 promoter produced twofold amounts of eGFP in comparison to clones expressing under the pGAP promoter with the same GCN in screening cultures.

TABLE 5 eGFP expression in screening cultures under the control of pGAP or pCS1 correlated to GCN. Per GCN, pCS1 clones express twice the amount of eGFP as pGAP clones.

| Clone | FL/Cell size | GCN | Fluorescence/Cell size/GCN |
|-------|--------------|-----|----------------------------|
| pGAP_eGFP#2 | 6.0 | 1 | 6.0 |
| pCS1_eGFP#4 | 13.0 | 1 | 13.0 | e) Analysis of pCS1 Promoter Strength in Fed-Batch Fermentation

To assess pCS1 promoter activity in production process-like conditions, fed batch cultivations of one pCS1 clone (pCS1_eGFP#4) and one pGAP clone (pGAP_eGFP#2) each harboring one copy of the eGFP expression cassette (see Example 2d) were performed.

Fed batch fermentations were performed in DASGIP reactors with a final working volume of 1.0 L.

Following media were used:

$PTM_1$ Trace Salts Stock Solution Contained Per Liter 6.0 g $CuSO_4 \cdot 5H_2O$, 0.08 g NaI, 3.36 g $MnSO_4 \cdot H_2O$, 0.2 g $Na_2MoO_4 \cdot 2H_2O$, 0.02 g $H_3BO_3$, 0.82 g $CoCl_2$, 20.0 g $ZnCl_2$, 65.0 g $FeSO_4 \cdot 7H_2O$, 0.2 g biotin and 5.0 ml $H_2SO_4$ (95%-98%).

Glycerol Batch Medium Contained Per Liter 2 g Citric acid monohydrate ($C_6H_8O_7 \cdot H_2O$), 39.2 g Glycerol, 12.6 g $NH_4H_2PO_4$, 0.5 g $MgSO_4 \cdot 7H_2O$, 0.9 g KCl, 0.022 g $CaCl_2 \cdot 2H_2O$, 0.4 mg biotin and 4.6 ml PTM1 trace salts stock solution. HCl was added to set the pH to 5.

Glucose Fed Batch Medium Contained Per Liter 464 g glucose monohydrate, 5.2 g $MgSO_4.7H_2O$, 8.4 g KCl, 0.28 g $CaCl_2.2H_2O$, 0.34 mg biotin and 10.1 mL PTM1 trace salts stock solution.

The dissolved oxygen was controlled at DO=20% with the stirrer speed (400-1200 rpm). Aeration rate was 24 L $h^{-1}$ air, the temperature was controlled at 25° C. and the pH setpoint of 5 was controlled with addition of $NH_4OH$ (25%).

To start the fermentation, 400 mL batch medium was sterile filtered into the fermenter and *P. pastoris* clone pCS1_eGFP#1 was inoculated (from pre-culture) with a starting optical density (OD600) of 1. The batch phase of approximately 25 h (reaching a dry biomass concentration of approximately 20 g/L) was followed by a glucose-limited fed batch starting with an exponential feed for 7 h and a constant feed rate of 15 g/L for 13 h, leading to a final dry biomass concentration of approximately 110 g/L. Samples were taken during batch and fed batch phase, and analyzed for eGFP expression using a plate reader (Infinite 200, Tecan, CH). Therefore, samples were diluted to an optical density (OD600) of 5. Fermentations were performed in duplicates. Results are shown in Table 6 as relative fluorescence per bioreactor (FL/r). The clone expressing under control of the pCS1 promoter had on average 4.2 fold higher eGFP expression compared to pGAP during the whole fermentation process.

TABLE 6

Relative fluorescence per bioreactor of two different *P. pastoris* clones expressing eGFP under the control of pGAP or pCS1 in an optimized fed batch fermentation. t indicates feed time.

|  | pGAP_eGFP#2 | | pCS1_eGFP#1 | | comparison FL/r |
|---|---|---|---|---|---|
| t [h] | FL/r | STDEV | FL/r | STDEV | pCS1/pGAP |
| −4.5 | 2.1 | 0.1 | 9.3 | 0.6 | 4.4 |
| 0.8 | 4.7 | 0.1 | 16.8 | 0.9 | 3.6 |
| 2.3 | 5.9 | 1.0 | 20.2 | 1.5 | 3.4 |
| 4.3 | 9.2 | 0.1 | 35.3 | 1.4 | 3.8 |
| 6.8 | 14.2 | 0.6 | 57.6 | 4.0 | 4.1 |
| 17.9 | 57.6 | 4.2 | 288.2 | 15.6 | 5.0 |
| 19.9 | 86.0 | 16.6 | 337.3 | 26.5 | 3.9 |
| 21.6 | 73.9 | 9.7 | 379.9 | 41.7 | 5.1 | f) Promoter Activity of pCS1 at Different Growth Conditions and Substrates

In order to gain more information about promoter activity of pCS1 on different media compositions and growth conditions, strain pCS1_eGFP#4 was cultivated in YP medium containing different carbon sources, at different pH values and in synthetic minimal medium. Samples were taken 24 and 48 hours after inoculation of the main culture and analyzed by flow cytometry as described in Example 2c.

A single colony of pCS1-eGFP#4 or pGAP-eGFP#2 as reference was inoculated in liquid YPG-Zeo medium (per liter: 20 g peptone, 10 g yeast extract, 12.6 g glycerol and 25 mg Zeocin) as pre-culture. After approximately 24 h the pre-culture was used to inoculate the main culture with an OD600 of 0.1 in 2 mL main culture medium. Main culture media were as follows: YP per liter: 20 g peptone, 10 g yeast extract, pH 7.0-7.5; YPD: YP+2% glucose, YPG: YP+2% glycerol; YPM: YP+1% methanol; YPE: YP+1% ethanol; YPfeed bead: YP+1 glucose feed bead (Kuhner, CH, diameter 6 mm); YPD ph4.5: YPD set to pH 4.5 with HCl; SCD: synthetic screening medium (per liter: 22 g glucose monohydrate, 22 g citric acid, 3.15 g $(NH_4)_2HPO_4$, 0.027 g $CaCl_2*2H_2O$, 0.9 g KCl, 0.5 g $MgSO_4*7H_2O$, 2 mL 500× biotin and 1.47 mL trace salts stock solution [per liter: 6 g $CuSO_4*5H_2O$, 0.08 g NaI, 3 g $MnSO_4*H_2O$, 0.2 g $Na_2MoO_4*2H_2O$, 0.02 g $H_3BO_3$, 0.5 g $CoCl_2$, 20 g $ZnCl_2$, 5 g $FeSO_4*7H_2O$ and 5 mL $H_2SO_4$]; pH set to 5 with 5M KOH; sterilized by filtration). All cultures except the one with the feed bead, were fed with 0.5% of the respective carbon source after 19 h and 43 h. Results of eGFP fluorescence per cell size are shown in Table 7.

On YPD, pCS1 expression levels exceed pGAP expression levels by 2-fold after 24 and 48 h, whereas on YPG pCS1 expression levels were 3.9 fold higher after 24 h and 24 h. Expression levels under control of the novel pCS1 promoter were even higher when using methanol or ethanol as carbon source, or when cultivated at pH 4.5 (Table 7).

TABLE 7

Relative eGFP fluorescence per cell size of *P. pastoris* clones pGAP_eGFP#2 or pCS1-eGFP#4 after 24 h and 48 h cultivation in different screening media. Mean values and SD of 2 cultivations are given.

| clone | Main culture medium | 24 h | 48 h |
|---|---|---|---|
| pGAP_eGFP#2 | YPD | 291.0 | 392.9 |
| pGAP_eGFP#2 | YPG | 194.8 | 393.0 |
| pCS1_eGFP#4 | YPD | 598.7 ± 6.4 | 890.2 ± 52.2 |
| pCS1_eGFP#4 | YPG | 770.8 ± 17.5 | 1521.4 ± 77.2 |
| pCS1_eGFP#4 | YP + glucose feed bead | 724.3 ± 4.6 | 1559.3 ± 28.3 |
| pCS1_eGFP#4 | YPM | 844.0 ± 25.4 | 1526.4 ± 65.3 |
| pCS1_eGFP#4 | YPE | 873.1 ± 16.0 | 1658.0 ± 344.4 |
| pCS1_eGFP#4 | YPD, pH 4.5 | 742.1 ± 62.8 | 1938.8 ± 62.9 |
| pCS1_eGFP#4 | SCD, pH 5.0 | 382.4 ± 11.5 | 1072.2 ± 167.1 |

Example 3: Comparative Promoter Activity Studies of the Newly Identified Promoter pCS1 in *P. pastoris* Using Human Serum Albumin (HSA) as Extracellular Expressed Reporter Gene In order to analyze the properties of the newly identified promoter for expression of the secreted reporter protein HSA, shake flask screenings were performed as follows: Pre-culture for 24 hours was done in rich medium containing glycerol as carbon source—simulating the batch phase of the process, which was followed by the main culture in buffered rich medium (2% glucose). The main culture was fed with 0.5% glucose every 12 hours.

a) Strain & Expression Vector

The *P. pastoris* wild type strain (CBS2612, CBS-KNAW Fungal Biodiversity Centre, Centraalbureau voor Schimmelcultures, Utrecht, The Netherlands) was used as host strain. Transformation of the strain was carried out with an in-house vector named pPUZZLE (Stadlmayr et al. J. Biotechnol 2010 December; 150(4):519-29), selection of positive transformants was based on the Zeocin resistance. For secretory expression of human serum albumin (HSA) its native secretion leader was used.

b) Amplification and Cloning of the Newly Identified Promoter pCS1 into an in-House Expression Vector The promoter amplified in Example 2b was cloned into the pPUZZLE expression vector pPM1aZ10_HSA, resulting in pPM1aZ10_pCS1_HSA. Additionally, the vector pPM1aZ10_pGAP_HSA, containing the commonly used promoter of glyceraldehyde 3-phosphate dehydrogenase promoter (pGAP) was used as reference. The promoters were inserted upstream of the start codon of the HSA gene using the ApaI and the SbfI restriction sites (see Table 3). The correctness of the promoter sequences was verified by Sanger sequencing.

c) Expression of HSA in *P. pastoris* Under Control of the Newly Identified Promoter pCS1

All plasmids were linearized using AscI restriction enzyme prior to electroporation (using a standard transformation protocol for *P. pastoris*) into *P. pastoris*. Selection of positive transformants was performed on YPD plates (per liter: 10 g yeast extract, 20 g peptone, 20 g glucose, 20 g agar-agar) plates containing 25 µg/mL of Zeocin. Colony PCR was used to ensure the presence of the transformed plasmid as described in Example 2c.

For HSA expression screening, a single colony was inoculated in liquid YPG-Zeo medium (per liter: 20 g peptone, 10 g yeast extract, 12.6 g glycerol and 25 mg Zeocin) as pre-culture. After approximately 24 h the pre-culture was used to inoculate the main culture with an OD600 of 0.1 in BM medium (per liter: 20 g peptone, 10 g yeast extract, 20 g glucose, 13.4 g yeast nitrogen base with ammonium sulfate, 0.4 mg biotin and 100 mM potassium phosphate buffer pH 6.0). The main culture was fed with 0.5% glucose every 12 hours. Samples were taken at the end of the main culture. Biomass concentration was determined by measuring OD600 or wet cell weight. HSA concentration in the culture supernatant was quantified by the Human Albumin ELISA Quantitation Set (Cat. No. E80-129, Bethyl Laboratories, TX, USA) following the supplier's instruction manual. The HSA standard was used with a starting concentration of 400 ng mL$^{-1}$. Samples were diluted accordingly in sample diluent (50 mM Tris-HCl, 140 mM NaCl, 1% (w/v) BSA, 0.05% (v/v) Tween20, pH 8.0). HSA titers from screening of clones expressing HSA under the control of pGAP (1 HSA gene copy) and of 9 clones expressing eGFP under the control of pCS1 are presented in Table 8. All pCS1-controlled clones secrete twice the amount of HSA as the pGAP-controlled clone with one gene copy. GCN of HSA were determined as described in Example 5. All analyzed clones under control of pCS1 harbored one copy of the expression cassette (1GCN). Thus, all clones under the control of the novel pCS1 promoter had a two-fold higher HSA secretion yield (mg secreted HSA/g biomass) than pGAP clones with the same GCN in screening cultures.

TABLE 8

Quantification of secreted HSA levels in supernatants of *P. pastoris* clones expressing HSA under the control of pGAP and pCS1 after 48 h screening culture.

| clone | HSA [mg/L] 48 h main culture |
|---|---|
| pGAP_HSA #3 (1GCN) | 32.8 |
| pCS1_HSA | 76.5 +/− 5.0 |

Example 4: Fed-Batch Cultivation of *P. pastoris* Strains Expressing HSA Under Control of the pCS1 Promoter To analyze the ability of pCS1 to drive expression of HSA in production process-like conditions, fed batch cultivations of one pCS1 clone (pCS1_HSA#1) harboring one copy of the HSA expression cassette (see Example 3) were performed.

The fermentations were performed in DASGIP bioreactors with a final working volume of 1.0 L. Two different *P. pastoris* strains expressing HSA under control of pGAP (pGAP_HSA#3 having one HSA gene copy, and pGAP_HSA#4 having two HSA gene copies, described in Prielhofer et al. 2013. Microb. Cell. Fact. 12:5) were cultivated as reference.

Following media were used:

PTM$_1$ Trace Salts Stock Solution Contained Per Liter 6.0 g CuSO$_4$.5H$_2$O, 0.08 g NaI, 3.36 g MnSO$_4$.H$_2$O, 0.2 g Na$_2$MoO$_4$.2H$_2$O, 0.02 g H$_3$BO$_3$, 0.82 g CoCl$_2$, 20.0 g ZnCl$_2$, 65.0 g FeSO$_4$.7H$_2$O, 0.2 g biotin and 5.0 ml H$_2$SO$_4$ (95%-98%).

Glycerol Batch Medium Contained Per Liter 39.2 g Glycerol, 27.9 g H$_3$PO$_4$ (85%), 7.8 g MgSO$_4$.7H$_2$O, 2.6 g KOH, 9.5 g K$_2$SO$_4$, 0.6 g CaSO$_4$.2H$_2$O, 0.4 mg biotin and 4.6 mL PTM1 trace salts stock solution. The pH was adjusted to 5.85 after sterile filtering into the fermenter.

Glucose Fed Batch Medium Contained Per Liter 550 g glucose monohydrate, 6.5 g MgSO$_4$.7H$_2$O, 10 g KCl, 0.35 g CaCl$_2$.2H$_2$O, 0.4 mg biotin and 12 mL PTM1 trace salts stock solution.

The dissolved oxygen was controlled at DO=20% with the stirrer speed (400-1200 rpm). Aeration rate is 24 L h$^{-1}$ air, the temperature was controlled at 25° C. and the pH setpoint of 5.85 is controlled with addition of NH$_4$OH (25%).

To start the fermentation, 400 mL batch medium was sterile filtered into the fermenter and *P. pastoris* was inoculated (from pre-culture) with a starting optical density (OD600) of 1. The batch phase of approximately 25 h reached a dry biomass concentration of approximately 20 g/L and was followed by a fed batch with constant feed of glucose medium (2 g L$^{-1}$ h$^{-1}$) for 100 hours, leading to a dry biomass concentration of approximately 100 g/L. The pH was 5.85 during batch, and kept at 5.85 throughout the fermentation. Samples were taken during batch and fed batch phase. HSA concentration was quantified using the Human Albumin ELISA Quantitation Set (Bethyl, Cat. No. E80-129) as described in Example 3c.

As shown previously, the pGAP clone with 2 HSA copies secreted twice as much as the pGAP clone with one copy (Prielhofer et al. 2013. Microb. Cell. Fact. 12:5). Two clones secreting HSA under control of pCS1 reached more than 4-fold higher HSA titers at the end of batch and fed batch compared to a single copy pGAP clone (results shown in Table 9). Correlated to biomass and GCN, the pCS1 clones produced 390% secreted HSA of the pGAP clone with the same gene copy number.

TABLE 9

Yeast dry mass concentrations and HSA titers in the supernatant at batch end and fed batch end, and HSA titer per yeast dry mass at fed batch end of bioreactor cultivations of *P. pastoris* clones expressing HSA under the control of pCS1 or pGAP.

| | | batch end | | fed batch end | | |
|---|---|---|---|---|---|---|
| Promoter | GCN | HSA [mg L$^{-1}$] | YDM [g L$^{-1}$] | HSA [mg L$^{-1}$] | YDM [g L$^{-1}$] | % HSA/YDM of P$_{GAP}$ |
| P$_{CS1}$#1 | 1 | 38.1 | 22.2 | 377.7 | 119.9 | 390.7 |
| P$_{GAP}$#3 | 1 | 8.4 | 22.1 | 78.6 | 97.7 | 100.0 |
| P$_{GAP}$#4 | 2 | 17.4 | 24.4 | 167.7 | 121.0 | 172.0 |

Example 5: Determination of Gene Copy Numbers (GCN) of Selected Clones

Expression strength is often correlated to the number of expression cassettes integrated into the *P. pastoris* genome.

Therefore the gene copy number of selected clones was determined. Genomic DNA was isolated using the DNeasy Blood&Tissue Kit (Quiagen, Cat. No. 69504). Gene copy numbers were determined using quantitative PCR. Therefore, SensiMix SYBR Kit (Bioline, QT605-05) was used. The Sensi Mix SYBR was mixed with the respective primers (given in Prielhofer et al. 2013. Microb. Cell. Fact. 12:5) and the sample, and applied for real time analysis in a real-time PCR cycler (Rotor Gene, Qiagen). All samples were analyzed in tri- or quadruplicates. Rotor Gene software was used for data analysis.

Example 6: Comparative Promoter Activity Studies of the Newly Identified Promoter pCS1 in *P. pastoris* Using Porcine Carboxypeptidase B (CpB) as Extracellular Expressed Reporter Gene In order to analyze the properties of the newly identified promoter, shake flask screenings are performed as follows: Pre-culture for 24 hours is done with rich medium containing glycerol as carbon source, which is followed by the main culture with rich media.

a) Strain & Expression Vector

The *P. pastoris* wild type strain (CBS2612, CBS-KNAW Fungal Biodiversity Centre, Centraalbureau voor Schimmelcultures, Utrecht, The Netherlands) is used as host strain. Transformation of the strain is carried out with an in-house vector named pPUZZLE (Stadlmayr et al. J. Biotechnol 2010 December; 150(4):519-29), selection of positive transformants is based on the Zeocin resistance. For secretory expression of porcine carboxypeptidase B (CpB) yeast alpha mating factor leader is used.

b) Amplification and Cloning of the Newly Identified Promoter pCS1 into an In-House Expression Vector The promoter amplified in Example 2b are cloned into the pPUZZLE expression vector pPM1aZ30_aMF_CpB, resulting in pPM1aZ30_pCS1_aMF_CpB. Additionally, the vector pPM1dZ30_pGAP_CpB, containing the commonly used promoter of glyceraldehyde 3-phosphate dehydrogenase promoter (pGAP) is used as reference. The promoters are inserted upstream of the start codon of the CpB gene using the ApaI and the SbfI restriction sites The correctness of the promoter sequences is verified by Sanger sequencing.

c) Expression of CpB in *P. pastoris* Under Control of the Newly Identified Glucose-Limit Induced Promoters Plasmids are linearized using AscI restriction enzyme prior to electroporation (using a standard transformation protocol for *P. pastoris*) into *P. pastoris*. Selection of positive transformants is performed on YPD plates (per liter: 10 g yeast extract, 20 g peptone, 20 g glucose, 20 g agar-agar) plates containing 25 µg/mL of Zeocin. Colony PCR is used to ensure the presence of the transformed plasmid as described in Example 2c.

For CpB expression screening, a single colony is inoculated in liquid YPG-Zeo medium (per liter: 20 g peptone, 10 g yeast extract, 12.6 g glycerol and 25 mg Zeocin) as pre-culture. After approximately 24 h the pre-culture is used to inoculate the main culture with an OD600 of 1 in YPD medium (per liter: 20 g peptone, 10 g yeast extract, 20 g glucose). Main culture is fed with 0.5% glucose every 12 hours. Samples are taken at the end of the pre-culture, and 24 and 48 hours after inoculation of the main culture. Biomass concentration is determined by measuring OD600 or wet cell weight. CpB concentration in the culture supernatant is quantified by an enzymatic assay, based on the conversion of hippuryl-L-arginine to hippuric acid by the CpB. Reaction kinetics are measured by monitoring the absorption at 254 nm at 25° C. using a Hitachi U-2910 Spectrophotometer when the reaction is started. Samples and standards are buffered with assay buffer (25 mM Tris, 100 mM HCl, pH 7.65) and are activated using activation buffer (0.01 mgL-1 Trypsin, 300 mM Tris, 1 µM $ZnCl_2$, pH 7.65). Activation buffer without trypsin is used instead of sample as negative control. The reaction is started by adding the substrate solution (1 mM hippuryl-L-arginine in assay buffer).

d) Fed-Batch Cultivation of *P. pastoris* Strains Expressing CpB Under Control of the pCS1 Promoter Fed Batch Fermentation is Done as Described in Example 4 Using Media as Described in Example 2d.

Example 7: Comparative Promoter Activity Studies of the Newly Identified Promoter pCS1 in *P. pastoris* Multicopy Clones Using Human Serum Albumin (HSA) as Extracellular Expressed Reporter Gene To investigate if HSA production could be further enhanced by higher GCN, $P_{CS1}$ clones expressing HSA were amplified by the post-transformational vector amplification method, as described by Marx et al., (2009). Vectors were generated that integrate into the rDNA locus by homologous recombination. The amplification was done by selection on stepwise increasing concentration of antibiotics.

a) Strain & Expression Vector

The *P. pastoris* wild type strain (CBS2612, CBS-KNAW Fungal Biodiversity Centre, Centraalbureau voor Schimmelcultures, Utrecht, The Netherlands) was used as host strain. Transformation of the strain was carried out with a variant of the vector pPUZZLE containing the NTS region of the ribosomal DNA locus as integration site (Marx et al. 2009. FEMS Yeast Res. 9(8):1260-70), selection of positive transformants was based on the Zeocin resistance. For secretory expression of human serum albumin (HSA) its native secretion leader was used.

The pCS1 promoter amplified in Example 2b was cloned into the pPUZZLE expression vector pPM1nZ30_HSA, resulting in pPM1nZ30_pCS1_HSA.

The promoter was inserted upstream of the start codon of the HSA gene using the ApaI and the SbfI restriction sites. The correctness of the promoter sequences was verified by Sanger sequencing.

b) Post-Transformational Vector Amplification and Expression of HSA in *P. pastoris* Under Control of the Newly Identified Promoter pCS1

Plasmids were linearized using SpeI restriction enzyme prior to electroporation (using a standard transformation protocol for *P. pastoris*) into *P. pastoris*. Initial selection of positive transformants was performed on YPD plates (per liter: 10 g yeast extract, 20 g peptone, 20 g glucose, 20 g agar-agar) plates containing 25 µg/mL of Zeocin. Colony PCR was used to ensure the presence of the transformed plasmid as described in Example 2c. Gene copy number amplification was done as described in Marx et al. (FEMS Yeast Res. 2009 December; 9(8):1260-70) by repeated streaking of clones on YPD agar plates containing higher Zeocin concentrations (50, 100 and 500 µg/mL Zeocin).

HSA expression screening and product quantification by HSA ELISA was performed as described in Example 3c. GCN was determined of some of the clones with the highest HSA secretion levels as described in Example 5. GCN-amplified $P_{CS1}$ clones and $P_{GAP}$ and $P_{CS1}$ clones with known GCNs (one or two) as control were cultivated in BM medium for 48 h.

By increasing HSA GCN, HSA secretion levels could also be increased (shown in Table 10). Multicopy clones expressing HSA under the control of pCS1 with 3 HSA gene copies produced two- to threefold higher amounts of HSA per WCW compared to the single copy clone. A similar increase in productivity of the multicopy pCS1 clones could also be expected in fed batch bioreactor cultivations as presented in Example 4.

TABLE 10

Screening results of HSA expression with single and multicopy clones under the control of pGAP or pCS1. GCN and titers per GCN are shown.

| Clone | µg HSA/g WCW | GCN | µg HSA/g WCW/GCN |
|---|---|---|---|
| pGAP_HSA#3 | 291.0 | 1 | 291.0 |
| pGAP_HSA#4 | 476.2 | 2 | 238.1 |
| pCS1_HSA#1 | 540.7 | 1 | 540.7 |
| pCS1_HSA#1_25-100#7 | 1464.1 | 3 | 488.0 |
| pCS1_HSA#1_50-100#5 | 1178.3 | 4 | 294.6 |
| pCS1_HSA#1_50-100#9 | 1580.7 | 3 | 526.9 |

Example 8: Comparative Promoter Activity Studies of the Newly Identified Promoter pCS1 in *P. pastoris* Using Antibody Fragment (Fab) as Extracellular Expressed Reporter Gene In order to analyze the properties of the newly identified promoter, shake flask screenings were performed as follows: Pre-culture for 24 hours was done with rich medium containing glycerol as carbon source, which was followed by the main culture with rich medium.

a) Strain & Expression Vector

The *P. pastoris* wild type strain (CBS2612, CBS-KNAW Fungal Biodiversity Centre, Centraalbureau voor Schimmelcultures, Utrecht, The Netherlands) was used as host strain. The pCS1 promoter amplified in Example 2b was cloned into the pPUZZLE expression vector containing either LC or Fab-HC of the HyHEL antibody as GOI. The promoter was inserted upstream of the start codon of the Fab genes using the ApaI and the SbfI restriction sites. After sequence verification, the expression cassettes for both chains were combined onto one vector by using the compatible restriction enzymes MreI and AgeI.

b) Expression of Fab in *P. pastoris* Under Control of the Newly Identified Promoter pCS1

Plasmids were linearized using AscI restriction enzyme prior to electroporation (using a standard transformation protocol for *P. pastoris*) into *P. pastoris*. Selection of positive transformants was performed on YPD plates (per liter: 10 g yeast extract, 20 g peptone, 20 g glucose, 20 g agar-agar) plates containing 25 µg/mL of Zeocin. Colony PCR was used to ensure the presence of the transformed plasmid as described in Example 2c.

Fab expression screening was performed similar to HSA expression screening described in Example 3c. Quantification of intact Fab was done by ELISA using anti-human IgG antibody (Abcam ab7497) as coating antibody (1:1,000), and a goat anti-Human Kappa Light Chains (Bound and Free)-alkaline phosphatase conjugated antibody (Sigma A3813) as detection antibody (1:1,000). Human Fab/Kappa, IgG fragment (Bethyl P80-115) was used as standard with a starting concentration of 50 ng/mL. Supernatant samples are diluted accordingly. Detection was done with pNPP substrate (Sigma S0942). Coating-, Dilution- and Washing buffer were based on PBS (2 mM $KH_2PO_4$, 10 mM $Na_2HPO_4 \cdot 2\ H_2O$, 2.7 mM g KCl, 8 mM NaCl, pH 7.4) and completed with BSA (1% (w/v)) and/or Tween20 (0.1% (v/v)) accordingly.

Genomic DNA from selected clones was isolated and GCNs of heavy chain (HC) and light chain (LC) were determined as described in Example 5. GCNs were related to clone PCS1#5, for which HC and LC GCN was set to one. Fab expression yields (µg Fab/g WCW), relative GCNs and Fab yield per GCN are shown in Table 11. As for the other model proteins, approximately two-times higher Fab yield per GCN (on average 35.4 µg Fab/gWCW) were obtained for clones expressing under control of pCS1 in comparison to clones expressing under control of pGAP.

TABLE 11

Screening results of Fab expression under the control of pGAP or pCS1. GCN and Fab yields per GCN are shown on the right.

| Clone | [µg Fab $g^{-1}$ WCW] | Relative GCN related to pCS1_Fab#5 | | Fab Yield [µg Fab $g^{-1}$ WCW] per GCN | |
|---|---|---|---|---|---|
| | | Heavy chain | Light chain | Heavy chain | Light chain |
| pGAP_Fab#34 | 73.3 | 4 | 3 | 18 | 24 |
| pCS1_Fab#2 | 35.9 | 1 | 1 | 36 | 36 |
| pCS1_Fab#4 | 66.8 | 2 | 2 | 33 | 33 |
| pCS1_Fab#5 | 34.7 | 1 | 1 | 34.7 | 34.7 |
| pCS1_Fab#7 | 37.5 | 1 | 1 | 38 | 37.5 | c) Fed-Batch Cultivation of *P. pastoris* Strains Expressing Fab Under Control of the pCS1 Promoter.

Fed batch fermentations were done similar as described in example 4 using media as described in example 2d.

In bioreactor cultivation Fab expression under the control of pCS1 resulted in more than 3.0-fold higher specific productivities (qP) per GCN compared to pGAP (see Table 12).

TABLE 12

Bioreactor cultivation results of Fab expression under the control of pGAP or pCS1. Fab yields at the end of the fed batch cultivation, mean specific productivity qP (average Fab production rate per biomass (dry cell weight DCW) over whole fed batch phase), relative GCN of the respective clones, and mean qP per GCN are shown.

| clone | Fab Yield [mg Fab $g^{-1}$ DCW] | qP [µg Fab $g^{-1}$ DCW $h^{-1}$] | Relative GCN related to pCS1_Fab#5 | | qP per GCN | |
|---|---|---|---|---|---|---|
| | | | Heavy chain | Light chain | Heavy chain | Light chain |
| pGAP_Fab#34 | 0.220 | 2.18 | 4 | 3 | 0.55 | 0.73 |
| pCS1_Fab#4 | 0.262 ± 0.000 | 3.51 ± 0.14 | 2 | 2 | 1.76 | 1.76 |
| pCS1_Fab#5 | 0.178 | 2.54 | 1 | 1 | 2.54 | 2.54 |

Example 9: Comparison of Variants of pCS1

Length variants of the pCS1 promoter are cloned as described in example 2a and screened similar as described in example 2c. Clones expressing under the control of pCS1 (standard length) and pGAP were used as controls. Forward primers and lengths of pCS1 and its variants are listed in Table 13.

TABLE 13 pCS1 and its variants: forward primers and lengths of the pCS1 size variants (SEQ ID 1)

| variants | forward primer | | Length (bp) |
|---|---|---|---|
| pCS1 (standard) SEQ ID 1 | GATAGGGCCCCAGGGCATCATTGAGGTTTCCAC SEQ ID 16 | | 985 |
| pCS1-1488 SEQ ID 2 | GATAGGGCCCGATAGTTCTAGAAGACCTGGCG TCG SEQ ID 17 | | 1488 |
| pCS1-767F SEQ ID 3 | GATAGGGCCCAGCCAACCATCTTTTGTTTCG SEQ ID 18 | | 767 |
| pCS1-500F SEQ ID 4 | GATAGGGCCCGTGGTTTCCAGGACAACACCC SEQ ID 19 | | 500 |
| pCS1-344F SEQ ID 5 | GATAGGGCCCGACCGCAATTCACCATGATGC SEQ ID 20 | | 344 |
| pCS1-234F SEQ ID 6 | GATAGGGCCCAGCCTGCTTCATTCCTGCC SEQ ID 21 | | 234 |
| pCS1-138F SEQ ID 7 | GATAGGGCCCCCGCGAAAAAGGTTTGTTTATAG SEQ ID 22 | | 138 |
| pCS1-85F SEQ ID 8 | GATAGGGCCCCATACTCTCCTCCCCCCCCTG SEQ ID 23 | | 85 |

Screenings of clones expressing eGFP under the control of pGAP, pCS1 or pCS1 revealed that pCS1 requires a minimal length of approximately 500 bp for optimal activity. Shorter pCS1 variants loose activity with decreasing length (see Table 14).

TABLE 14

Screening results (relative fluorescence) of eGFP expression under the control of pGAP, pCS1 or pCS1 variants.

| Clone | FL/Cell size, 24 h | FL/Cell size, 48 h |
|---|---|---|
| pGAP_eGFP#2 | 15.39 | 17.59 |
| pCS1_eGFP#4 | 25.30 | 37.77 |
| pCS1_85pool | −0.15 | 0.04 |
| pCS1_138pool | 7.70 | 6.30 |
| pCS1_234pool | 18.57 | 19.71 |
| pCS1_344pool | 25.19 | 27.63 |
| pCS1_500pool | 28.50 | 38.82 |
| pCS1_767pool | 26.88 | 36.47 |
| pCS1_1488pool | 30.59 | 44.40 |

Example 10: Verification of Expression Strength of a Promoter in a Clone Expressing eGFP Under Control of Said Promoter in Growth-Limited Conditions at High and Low Growth Rates a) Strain A host strain (e.g. *Pichia pastoris*) expressing eGFP under control of a "promoter of Interest" and a strain expressing eGFP under control of pGAP are used to compare expression levels.

b) Cultivation of eGFP Expressing Strains for Promoter Comparison

These strains are cultivated in chemostat at two fixed specific growth rates (one low, one high specific growth rate by setting the dilution rate), using DASGIP bioreactors with a final working volume of 1.0 L.

Following media are used:
PTM1 Trace Salts Stock Solution Contains Per Liter
6.0 g $CuSO_4.5H_2O$, 0.08 g NaI, 3.36 g $MnSO_4.H_2O$, 0.2 g $Na_2MoO_4.2H_2O$,
0.02 g $H_3BO_3$, 0.82 g $CoCl_2$, 20.0 g $ZnCl_2$, 65.0 g $FeSO_4.7H_2O$, 0.2 g biotin and 5.0 ml $H_2SO_4$ (95%-98%).
Glycerol Batch Medium Contains Per Liter
2 g Citric acid monohydrate ($C_6H_8O_7.H2O$), 39.2 g Glycerol, 12.6 g $NH_4H_2PO_4$,
0.5 g $MgSO_4.7H_2O$, 0.9 g KCl, 0.022 g $CaCl_2.2H_2O$, 0.4 mg biotin and 4.6 ml PTM1
trace salts stock solution. HCl is added to set the pH to 5.
Chemostat Medium Contains Per Liter
2.5 g Citric acid monohydrate ($C_6H_8O_7.H_2O$), 55.0 g glucose monohydrate, 21.75 g $(NH_4)_2HPO_4$, 1.0 g $MgSO_4.7H_2O$, 2.5 g KCl, 0.04 g $CaCl_2.2H_2O$, 0.4 mg biotin and 2.43 mL PTM1 trace salts stock solution. HCl is added to set the pH to 5.

The dissolved oxygen is controlled at DO=20% with the stirrer speed (400-1200 rpm). Aeration rate is 24 L h-1 air, the temperature is controlled at 25° C. and the pH setpoint of 5 is controlled with addition of NH4OH (25%). To start the fermentation, 400 mL batch medium is sterile filtered into the fermenter and a *P. pastoris* clone is inoculated (from pre-culture) with a starting optical density (OD600) of 1. The batch phase of approximately 25 h (reaching a dry biomass concentration of approximately 20 g L-1) is followed by glucose-limited chemostat cultivation. The feed rate of chemostat medium and the harvest rate are used to keep a constant specific growth rate as desired. During this cultivation, culture broth volume is kept constant and cell dry weight is determined in order to ensure a constant growth rate. Cells are cultivated at a high and low growth rate of 0.15 and 0.015 $h^{-1}$, respectively. Therefore, the feed/harvest rate is controlled at 150 mL $h^{-1}$ $L^{-1}$ (mL chemostat medium per liter culture broth and hour) and 15 mL $h^{-1}$ 5 $L^{-1}$, respectively.

c) Sampling

Samples are taken in steady state conditions (after at least 5 volume exchanges) and analyzed for eGFP expression using a plate reader (Infinite 200, Tecan, CH). Therefore, samples are diluted to an optical density (OD600) of 5. Fermentations are performed in duplicates. Expression data is compared by calculating relative fluorescence per bioreactor as described in example 2d).

Example 11: Identification of a *P. pastoris* Promoter Enabling High Transcription at High and Low Specific Growth Rates In order to identify a promoter enabling high transcription at high and low growth rates, analysis of gene expression patterns was done using DNA microarrays. Genes displaying high transcription strength at high and low growth rates were selected from the transcriptomics data. Therefore, *P. pastoris* cells were grown in chemostat cultivation as described in example 10b) at high and low specific growth rates of 0.15 and 0.015 $h^{-1}$, respectively. Sampling, RNA purification, sample preparation for microarray hybridization, microarray analysis, data acquisition and statistical evaluation are done as described in example 1c), 1d), 1e) and 1f). Genes and respective promoters with high transcription strength at high and low growth rate were identified by browsing the microarray data for genes with high signal intensities in both, high and low growth rate conditions. As a second criterion, signal intensities should be higher than those of the glyceraldehyde-3-phosphate dehydrogenase (GAP, synonyms GAPDH and TDH3) gene in both conditions. To isolate the promoter, a nucleic acid fragment of approximately 1000 bps upstream of the start codon ATG of the respective gene was amplified.

The invention claimed is:

1. An expression construct comprising a pCS1 promoter which is any of:
   i) a promoter comprising the nucleic acid sequence identified as SEQ ID NO: 1, or
   ii) a promoter which is a size variant of SEQ ID NO: 1 comprising a contiguous fragment of SEQ ID NO: 1 that has a length of at least 500 bp and includes the 3' terminus of SEQ ID NO: 1 wherein the size variant has at least 80% sequence identity to the contiguous fragment of SEQ ID NO: 1, which pCS1 promoter is operably linked to a nucleotide sequence encoding a protein of interest (POI), which pCS1 promoter is not natively associated with the nucleotide sequence encoding the POI.

2. The expression construct according to claim 1, wherein the pCS1 promoter consists of SEQ ID NO: 1.

3. The expression construct according to claim 1, wherein the promoter is selected from the group consisting of
   i) homologs obtainable by modifying the nucleotide sequence of SEQ ID NO: 1 or size variants thereof, by insertion, deletion or substitution of one or more nucleotides within the sequence or at either or both of the distal ends of the sequence; and
   ii) analogs derived from species other than *Pichia pastoris*.

4. The expression construct according to claim 1, which further comprises a nucleic acid sequence encoding a signal peptide enabling the secretion of the POI.

5. A recombinant host cell which comprises the expression construct according to claim 1.

6. The recombinant host cell according to claim 5, comprising multiple copies of the expression construct of claim 1.

7. The recombinant host cell according to claim 5, which is selected from the group consisting of mammalian, insect, yeast, filamentous fungi and plant cells.

8. A stable culture of a plurality of the cell according to claim 5.

9. The expression construct according to claim 1, wherein the promoter comprises a nucleic acid sequence selected from the group consisting of SEQ ID NO: 2, 3, 4, 5, and 6.

10. The expression construct according to claim 4, wherein the nucleic acid sequence encoding the signal peptide is located adjacent to the 5' end of the nucleotide sequence encoding the POI.

11. A method of producing a POI by culturing a recombinant host cell line comprising the promoter according to claim 1, and a nucleic acid encoding the POI under the transcriptional control of said promoter, comprising the steps of
   a) cultivating the cell line under conditions to express said POI, and
   b) recovering the POI.

12. The method according to claim 11, wherein the POI is expressed under growth-limiting conditions.

13. The method according to claim 11, wherein the cell line is cultivated under batch, fed-batch or continuous cultivation conditions, and/or in media containing limited carbon substrate.

14. The method according to claim 13, wherein the cultivation is performed in a bioreactor starting with a batch phase followed by a fed-batch phase or a continuous cultivation phase.

15. The method according to claim 11, wherein the POI is a heterologous protein.

* * * * *

SEQUENCE LISTING

<160> NUMBER OF SEQ ID NOS: 24

<210> SEQ ID NO 1
<211> LENGTH: 985
<212> TYPE: DNA
<213> ORGANISM: Pichia pastoris

<400> SEQUENCE: 1

| | | | | | |
|---|---|---|---|---|---|
| agggcatcat | tgaggtttcc | acaaaaggaa | gaaacatgga | tccagagaca | tcaacagaga | 60 |
| ggaaagcggg | tagtgaagcc | gaagccacaa | cacagcccga | tttggaaggg | agttcacaat | 120 |
| caaggtgagt | ccagccattt | tttttctttt | ttttttttt | attcaggtga | acccacctaa | 180 |
| ctatttttaa | ctgggatcca | gtgagctcgc | tgggtgaaag | ccaaccatct | tttgtttcgg | 240 |
| ggaaccgtgc | tcgccccgta | agttaattt | ttttttcccg | cgcagcttta | atctttcggc | 300 |
| agagaaggcg | ttttcatcgt | agcgtgggaa | cagaataatc | agttcatgtg | ctatacaggc | 360 |
| acatggcagc | agtcactatt | tgcttttta | accttaaagt | cgttcatcaa | tcattaactg | 420 |
| accaatcaga | ttttttgcat | ttgccactta | tctaaaaata | cttttgtatc | tcgcagatac | 480 |
| gttcagtggt | ttccaggaca | acacccaaaa | aaaggtatca | atgccactag | gcagtcggtt | 540 |
| ttatttttgg | tcacccacgc | aaagaagcac | ccacctcttt | taggttttaa | gttgtgggaa | 600 |
| cagtaacacc | gcctagagct | tcaggaaaaa | ccagtacctg | tgaccgcaat | tcaccatgat | 660 |
| gcagaatgtt | aatttaaacg | agtgccaaat | caagatttca | acagacaaat | caatcgatcc | 720 |
| atagttaccc | attccagcct | tttcgtcgtc | gagcctgctt | cattcctgcc | tcaggtgcat | 780 |
| aactttgcat | gaaaagtcca | gattagggca | gattttgagt | ttaaaatagg | aaatataaac | 840 |
| aaatataccg | cgaaaaaggt | ttgtttatag | cttttcgcct | ggtgccgtac | ggtataaata | 900 |
| catactctcc | tcccccccct | ggttctcttt | ttcttttgtt | acttacattt | taccgttccg | 960 |
| tcactcgctt | cactcaacaa | caaaa | | | | 985 |

<210> SEQ ID NO 2
<211> LENGTH: 1488
<212> TYPE: DNA
<213> ORGANISM: Pichia pastoris

<400> SEQUENCE: 2

| | | | | | |
|---|---|---|---|---|---|
| gatagttcta | gaagacctgg | cgtcgctggt | caactactcg | tttcacaagt | tgacaaagac | 60 |
| ttttaccaag | agaagagcag | ttgtcaccga | ccacaataac | aacctggaag | ccgagaaaaa | 120 |
| acttggaatc | tccaaggtga | gactgcctag | aaatccgtac | tctgcggccg | atcgaagact | 180 |
| gcatttcctc | caagaattga | tgctcatggt | ctcatcttac | aatcgcacac | acaacagtgt | 240 |
| cagtcttctt | tgcggtccct | tgaacacaac | caaccgaaag | gtggggaagt | ctaatgtcac | 300 |
| gcaaacgata | ttgcaaccaa | tgttgggctc | tactggcgtc | tggctgcatc | aaatagctga | 360 |
| tcggttcgta | atcttcaaag | attggtgtag | gacgaacgag | tctgctgggc | tacaagtttt | 420 |
| gccccatatc | gctgttcaag | ccaacccgcg | gaatcccaaa | acaccccatc | cgacaaaagt | 480 |
| tgttgttttc | agcagatcta | gggagggcat | cattgaggtt | tccacaaaag | gaagaaacat | 540 |
| ggatccagag | acatcaacag | agaggaaagc | gggtagtgaa | gccgaagcca | caacacagcc | 600 |
| cgatttggaa | gggagttcac | aatcaaggtg | agtccagcca | ttttttttct | ttttttttt | 660 |
| tttattcagg | tgaacccacc | taactatttt | taactgggat | ccagtgagct | cgctgggtga | 720 |
| aagccaacca | tctttgtt | cggggaaccg | tgctcgcccc | gtaagttaa | tttttttttc | 780 |
| ccgcgcagct | ttaatctttc | ggcagagaag | gcgttttcat | cgtagcgtgg | gaacagaata | 840 |

```
atcagttcat gtgctataca ggcacatggc agcagtcact attttgcttt ttaaccttaa    900
agtcgttcat caatcattaa ctgaccaatc agatttttg catttgccac ttatctaaaa    960
atacttttgt atctcgcaga tacgttcagt ggtttccagg acaacaccca aaaaaggta   1020 tcaatgccac taggcagtcg gttttatttt tggtcaccca cgcaaagaag cacccacctc   1080
ttttaggttt taagttgtgg gaacagtaac accgcctaga gcttcaggaa aaaccagtac   1140
ctgtgaccgc aattcaccat gatgcagaat gttaatttaa acgagtgcca atcaagatt   1200 tcaacagaca aatcaatcga tccatagtta cccattccag ccttttcgtc gtcgagcctg   1260
cttcattcct gcctcaggtg cataactttg catgaaaagt ccagattagg gcagattttg   1320
agtttaaaat aggaaatata acaaatata ccgcgaaaaa ggtttgttta tagcttttcg   1380
cctggtgccg tacggtataa atacatactc tcctccccc cctggttctc ttttctttt   1440 gttacttaca ttttaccgtt ccgtcactcg cttcactcaa caacaaaa                1488

<210> SEQ ID NO 3
<211> LENGTH: 767
<212> TYPE: DNA
<213> ORGANISM: Pichia pastoris

<400> SEQUENCE: 3
agccaaccat cttttgtttc ggggaaccgt gctcgccccg taaagttaat tttttttcc     60 cgcgcagctt taatctttcg gcagagaagg cgttttcatc gtagcgtggg aacagaataa    120
tcagttcatg tgctatacag gcacatggca gcagtcacta ttttgctttt taaccttaaa    180
gtcgttcatc aatcattaac tgaccaatca gattttttgc atttgccact tatctaaaaa    240
tacttttgta tctcgcagat acgttcagtg gtttccagga caacacccaa aaaaggtat    300 caatgccact aggcagtcgg ttttattttt ggtcacccac gcaaagaagc acccacctct    360
tttaggtttt aagttgtggg aacagtaaca ccgcctagag cttcaggaaa accagtacc    420 tgtgaccgca attcaccatg atgcagaatg ttaatttaaa cgagtgccaa atcaagattt    480
caacagacaa atcaatcgat ccatagttac ccattccagc cttttcgtcg tcgagcctgc    540
ttcattcctg cctcaggtgc ataactttgc atgaaaagtc cagattaggg cagattttga    600
gtttaaaata ggaaatataa acaaatatac cgcgaaaaag gtttgtttat agcttttcgc    660
ctggtgccgt acggtataaa tacatactct cctccccccc ctggttctct ttttcttttg    720
ttacttacat tttaccgttc cgtcactcgc ttcactcaac aacaaaa                  767

<210> SEQ ID NO 4
<211> LENGTH: 500
<212> TYPE: DNA
<213> ORGANISM: Pichia pastoris

<400> SEQUENCE: 4
gtggtttcca ggacaacacc caaaaaaagg tatcaatgcc actaggcagt cggtttttatt     60 tttggtcacc cacgcaaaga agcacccacc tcttttaggt tttaagttgt gggaacagta    120
acaccgccta gagcttcagg aaaaaccagt acctgtgacc gcaattcacc atgatgcaga    180
atgttaattt aaacgagtgc caaatcaaga tttcaacaga caaatcaatc gatccatagt    240
tacccattcc agccttttcg tcgtcgagcc tgcttcattc ctgcctcagg tgcataactt    300
tgcatgaaaa gtccagatta gggcagattt tgagtttaaa ataggaaata taaacaaata    360
taccgcgaaa aaggtttgtt tatagctttt cgcctggtgc cgtacggtat aaatacatac    420
```

```
tctcctcccc ccctggttc tcttttttctt tgttacttta catttaccg ttccgtcact      480 cgcttcactc aacaacaaaa                                                  500

<210> SEQ ID NO 5
<211> LENGTH: 344
<212> TYPE: DNA
<213> ORGANISM: Pichia pastoris

<400> SEQUENCE: 5
gaccgcaatt caccatgatg cagaatgtta atttaaacga gtgccaaatc aagatttcaa     60
cagacaaatc aatcgatcca tagttaccca ttccagcctt tcgtcgtcg agcctgcttc     120 attcctgcct caggtgcata actttgcatg aaaagtccag attagggcag attttgagtt    180
taaaatagga aatataaaca aatataccgc gaaaaaggtt tgtttatagc ttttcgcctg    240
gtgccgtacg gtataaatac atactctcct ccccccctg gttctctttt tcttttgtta    300
cttacatttt accgttccgt cactcgcttc actcaacaac aaaa                     344

<210> SEQ ID NO 6
<211> LENGTH: 234
<212> TYPE: DNA
<213> ORGANISM: Pichia pastoris

<400> SEQUENCE: 6
agcctgcttc attcctgcct caggtgcata actttgcatg aaaagtccag attagggcag     60
attttgagtt taaaatagga aatataaaca aatataccgc gaaaaaggtt tgtttatagc    120
ttttcgcctg gtgccgtacg gtataaatac atactctcct ccccccctg gttctcttt    180 tcttttgtta cttacatttt accgttccgt cactcgcttc actcaacaac aaaa          234

<210> SEQ ID NO 7
<211> LENGTH: 138
<212> TYPE: DNA
<213> ORGANISM: Pichia pastoris

<400> SEQUENCE: 7
ccgcgaaaaa ggtttgttta tagcttttcg cctggtgccg tacggtataa atacatactc     60
tcctcccccc cctggttctc ttttctttt gttacttaca ttttaccgtt ccgtcactcg    120
cttcactcaa caacaaaa                                                  138

<210> SEQ ID NO 8
<211> LENGTH: 85
<212> TYPE: DNA
<213> ORGANISM: Pichia pastoris

<400> SEQUENCE: 8
catactctcc tcccccccct ggttctcttt ttcttttgtt acttacattt taccgttccg     60
tcactcgctt cactcaacaa caaaa                                           85

<210> SEQ ID NO 9
<211> LENGTH: 408
<212> TYPE: DNA
<213> ORGANISM: Pichia pastoris

<400> SEQUENCE: 9
atgcaattct ctatcgtcgc tactttggct cttgctggtt ccgctctggc tgcttactct     60
aacgtaactt acacttacga gactaccatc accgatgttg tcaccgagct caccacttac    120
tgcccagagc caaccaccct cgttcacaag aacaagacca tcactgtgac cgccccaacc    180
```

```
actttgacca tcactgactg tccttgcacc atctccaaga ccaccaagat caccactgat    240
gttccaccaa ccaccactc caccccacac accaccacca ctcacgtgcc atctacctct     300
accccagctc caacccactc tgtttctacc atctctcacg gtggtgctgc taaggctggt    360
gttgctggtt tggccggtgt tgctgctgcc gctgcttact tcttgtaa                408
```

<210> SEQ ID NO 10
<211> LENGTH: 135
<212> TYPE: PRT
<213> ORGANISM: Pichia pastoris

<400> SEQUENCE: 10

```
Met Gln Phe Ser Ile Val Ala Thr Leu Ala Leu Ala Gly Ser Ala Leu
1               5                   10                  15

Ala Ala Tyr Ser Asn Val Thr Tyr Thr Tyr Glu Thr Thr Ile Thr Asp
            20                  25                  30

Val Val Thr Glu Leu Thr Thr Tyr Cys Pro Glu Pro Thr Thr Phe Val
        35                  40                  45

His Lys Asn Lys Thr Ile Thr Val Thr Ala Pro Thr Thr Leu Thr Ile
    50                  55                  60

Thr Asp Cys Pro Cys Thr Ile Ser Lys Thr Thr Lys Ile Thr Thr Asp
65                  70                  75                  80

Val Pro Pro Thr Thr His Ser Thr Pro His Thr Thr Thr Thr His Val
                85                  90                  95

Pro Ser Thr Ser Thr Pro Ala Pro Thr His Ser Val Ser Thr Ile Ser
            100                 105                 110

His Gly Gly Ala Ala Lys Ala Gly Val Ala Gly Leu Ala Gly Val Ala
        115                 120                 125

Ala Ala Ala Ala Tyr Phe Leu
    130                 135
```

<210> SEQ ID NO 11
<211> LENGTH: 402
<212> TYPE: DNA
<213> ORGANISM: Pichia pastoris

<400> SEQUENCE: 11

```
atgcaattct ctatcgtcgc tactttggct cttgctggtt ccgctctggc tgcttactct     60
aacgtaactt acacttacga gactaccatc accgatgttg tcactgagtt gaccacttac    120
tgcccagagc caaccacctt tgtttacaag aacaagacca tcaccgtgac tgagccaacc    180
actttgacca tcactgactg cccatgcacc atctcaaaga ccaccaagat caccactgat    240
gttccaccaa ccaccacgt cacccccatcc accactcacg tgccatctac ctctaccccca    300 gctccaaccc actctgtttc taccatctct cacggtggtg ctgctaaggc tggtgttgct    360
ggtttggccg tgttgctgc tgccgctgct tacttcttgt aa                        402
```

<210> SEQ ID NO 12
<211> LENGTH: 133
<212> TYPE: PRT
<213> ORGANISM: Pichia pastoris

<400> SEQUENCE: 12

```
Met Gln Phe Ser Ile Val Ala Thr Leu Ala Leu Ala Gly Ser Ala Leu
1               5                   10                  15

Ala Ala Tyr Ser Asn Val Thr Tyr Thr Tyr Glu Thr Thr Ile Thr Asp
            20                  25                  30
```

Val Val Thr Glu Leu Thr Thr Tyr Cys Pro Glu Pro Thr Thr Phe Val
        35                  40                  45

Tyr Lys Asn Lys Thr Ile Thr Val Thr Glu Pro Thr Thr Leu Thr Ile
    50                  55                  60

Thr Asp Cys Pro Cys Thr Ile Ser Lys Thr Lys Ile Thr Thr Asp
65                  70                  75                  80

Val Pro Pro Thr Thr His Val Thr Pro Ser Thr Thr His Val Pro Ser
                85                  90                  95

Thr Ser Thr Pro Ala Pro Thr His Ser Val Ser Thr Ile Ser His Gly
            100                 105                 110

Gly Ala Ala Lys Ala Gly Val Ala Gly Leu Ala Gly Val Ala Ala Ala
            115                 120                 125

Ala Ala Tyr Phe Leu
    130

<210> SEQ ID NO 13
<211> LENGTH: 491
<212> TYPE: DNA
<213> ORGANISM: Pichia pastoris

<400> SEQUENCE: 13
cttttttgta gaaatgtctt ggtgtcctcg tccaatcagg tagccatctc tgaaatatct      60
ggctccgttg caactccgaa cgacctgctg caacgtaaa attctccggg gtaaaactta     120
aatgtggagt aatggaacca gaaacgtctc ttcccttctc tctccttcca ccgcccgtta    180
ccgtccctag gaaattttac tctgctggag agcttcttct acggccccct tgcagcaatg    240
ctcttcccag cattacgttg cgggtaaaac ggaggtcgtg tacccgacct agcagcccag    300
ggatggaaaa gtcccggccg tcgctggcaa taatagcggg cggacgcatg tcatgagatt    360
attggaaacc accagaatcg aatataaaag gcgaacacct ttcccaattt tggtttctcc    420
tgacccaaag actttaaatt taatttattt gtccctattt caatcaattg aacaactatc    480
acctgcaggc c                                                        491

<210> SEQ ID NO 14
<211> LENGTH: 33
<212> TYPE: DNA
<213> ORGANISM: artificial
<220> FEATURE:
<223> OTHER INFORMATION: Primer

<400> SEQUENCE: 14
gatagggccc cagggcatca ttgaggtttc cac                                  33

<210> SEQ ID NO 15
<211> LENGTH: 36
<212> TYPE: DNA
<213> ORGANISM: artificial
<220> FEATURE:
<223> OTHER INFORMATION: Primer

<400> SEQUENCE: 15
gatacctgca ggttttgttg ttgagtgaag cgagtg                               36

<210> SEQ ID NO 16
<211> LENGTH: 33
<212> TYPE: DNA
<213> ORGANISM: artificial
<220> FEATURE:
<223> OTHER INFORMATION: Primer

```
<400> SEQUENCE: 16
gatagggccc cagggcatca ttgaggtttc cac                           33

<210> SEQ ID NO 17
<211> LENGTH: 35
<212> TYPE: DNA
<213> ORGANISM: artificial
<220> FEATURE:
<223> OTHER INFORMATION: Primer

<400> SEQUENCE: 17
gatagggccc gatagttcta gaagacctgg cgtcg                         35

<210> SEQ ID NO 18
<211> LENGTH: 31
<212> TYPE: DNA
<213> ORGANISM: artificial
<220> FEATURE:
<223> OTHER INFORMATION: Primer

<400> SEQUENCE: 18
gatagggccc agccaaccat cttttgtttc g                             31

<210> SEQ ID NO 19
<211> LENGTH: 31
<212> TYPE: DNA
<213> ORGANISM: artificial
<220> FEATURE:
<223> OTHER INFORMATION: Primer

<400> SEQUENCE: 19
gatagggccc gtggtttcca ggacaacacc c                             31

<210> SEQ ID NO 20
<211> LENGTH: 31
<212> TYPE: DNA
<213> ORGANISM: artificial
<220> FEATURE:
<223> OTHER INFORMATION: Primer

<400> SEQUENCE: 20
gatagggccc gaccgcaatt caccatgatg c                             31

<210> SEQ ID NO 21
<211> LENGTH: 29
<212> TYPE: DNA
<213> ORGANISM: artificial
<220> FEATURE:
<223> OTHER INFORMATION: Primer

<400> SEQUENCE: 21
gatagggccc agcctgcttc attcctgcc                                29

<210> SEQ ID NO 22
<211> LENGTH: 33
<212> TYPE: DNA
<213> ORGANISM: artificial
<220> FEATURE:
<223> OTHER INFORMATION: Primer

<400> SEQUENCE: 22
gatagggccc ccgcgaaaaa ggtttgttta tag                           33

<210> SEQ ID NO 23
```

```
<211> LENGTH: 31
<212> TYPE: DNA
<213> ORGANISM: artificial
<220> FEATURE:
<223> OTHER INFORMATION: Primer

<400> SEQUENCE: 23
gatagggccc catactctcc tcccccccct g                               31

<210> SEQ ID NO 24
<211> LENGTH: 345
<212> TYPE: DNA
<213> ORGANISM: artificial
<220> FEATURE:
<223> OTHER INFORMATION: translational fusion partner

<400> SEQUENCE: 24
ggccattacg gccgggggac ttacatttta ccgttccgtc actcgcttca ctcaacaaca    60
aaaatgcaat tctctatcgt cgctactttg gctcttgctg gttccgctct ggctgcttac   120
tctaacgtaa cttacactta cgagactacc atcaccgatg ttgtcaccga gctcaccact   180
tactgcccag agccaaccac cttcgttcac aagaacaaga ccatcactgt gaccgcccca   240
accactttga ccatcactga ctgtccttgc accatctcca agaccaccaa gatcaccact   300
gatgttccac caaccaccca ctccacccca ctggccgcct cggcc                  345
```